US008289381B2

(12) United States Patent
Bayer et al.

(10) Patent No.: US 8,289,381 B2
(45) Date of Patent: Oct. 16, 2012

(54) ENDOSCOPE WITH AN IMAGING CATHETER ASSEMBLY AND METHOD OF CONFIGURING AN ENDOSCOPE

(75) Inventors: Lex Bayer, Palo Alto, CA (US); Rupesh Desai, San Jose, CA (US); John Higgins, Los Altos, CA (US)

(73) Assignee: Avantis Medical Systems, Inc., Sunnyvale, CA (US)

( * ) Notice: Subject to any disclaimer, the term of this patent is extended or adjusted under 35 U.S.C. 154(b) by 1555 days.

(21) Appl. No.: 11/672,020

(22) Filed: Feb. 6, 2007

(65) Prior Publication Data

US 2007/0177008 A1 Aug. 2, 2007

Related U.S. Application Data

(63) Continuation-in-part of application No. 11/626,189, filed on Jan. 23, 2007, and a continuation-in-part of application No. 11/609,838, filed on Dec. 12, 2006, and a continuation-in-part of application No. 11/215,660, filed on Aug. 29, 2005, and a continuation-in-part of application No. 11/030,559, filed on Jan. 5, 2005, now abandoned.

(60) Provisional application No. 60/771,099, filed on Feb. 6, 2006.

(51) Int. Cl.
*H04N 7/18* (2006.01)
*A61B 1/00* (2006.01)
*A61B 1/06* (2006.01)

(52) U.S. Cl. ............................ 348/65; 600/113; 600/173

(58) Field of Classification Search ...................... 348/65
See application file for complete search history.

(56) References Cited

U.S. PATENT DOCUMENTS

| 3,437,747 | A | 4/1969 | Sheldon |
| 3,610,231 | A | 10/1971 | Takahashi et al. |
| 3,643,653 | A | 2/1972 | Takahashi et al. |
| 3,739,770 | A | 6/1973 | Mori |
| 3,889,662 | A | 6/1975 | Mitsui |
| 3,897,775 | A | 8/1975 | Furihata |
| 3,918,438 | A | 11/1975 | Hayamizu et al. |
| 4,261,344 | A | 4/1981 | Moore et al. |
| 4,351,587 | A | 9/1982 | Matsuo et al. |
| 4,398,811 | A | 8/1983 | Nishioka et al. |
| 4,494,549 | A | 1/1985 | Namba et al. |
| 4,573,450 | A | 3/1986 | Arakawa |
| 4,586,491 | A | 5/1986 | Carpenter |
| 4,625,236 | A | 11/1986 | Fujimori et al. |

(Continued)

FOREIGN PATENT DOCUMENTS

CN 1 628 603 6/2005

(Continued)

OTHER PUBLICATIONS

Advisory Action mailed on Nov. 2, 2010, for U.S. Appl. No. 11/609,838, filed Dec. 12, 2006, 3 pages.

(Continued)

*Primary Examiner* — Yves Dalencourt
*Assistant Examiner* — Hee Soo Kim
(74) *Attorney, Agent, or Firm* — Morrison & Foerster LLP

(57) ABSTRACT

An endoscope includes an insertion tube having an end, and an imaging catheter assembly. The imaging catheter assembly includes a tubular body, an imaging device, and a shape memory link that connects the imaging device to the tubular body.

12 Claims, 10 Drawing Sheets

U.S. PATENT DOCUMENTS

| | | |
|---|---|---|
| 4,646,722 A | 3/1987 | Silverstein et al. |
| 4,699,463 A | 10/1987 | D'Amelio et al. |
| 4,721,097 A | 1/1988 | D'Amelio |
| 4,727,859 A | 3/1988 | Lia |
| 4,741,326 A | 5/1988 | Sidall et al. |
| 4,790,295 A | 12/1988 | Tashiro |
| 4,800,870 A | 1/1989 | Reid, Jr. |
| 4,825,850 A | 5/1989 | Opie et al. |
| 4,836,211 A | 6/1989 | Sekino et al. |
| 4,846,154 A | 7/1989 | MacAnally et al. |
| 4,852,551 A | 8/1989 | Opie et al. |
| 4,853,773 A | 8/1989 | Hibino et al. |
| 4,862,873 A | 9/1989 | Yajima et al. |
| 4,867,138 A | 9/1989 | Kubota et al. |
| 4,869,238 A | 9/1989 | Opie et al. |
| 4,870,488 A | 9/1989 | Ikuno et al. |
| 4,873,572 A | 10/1989 | Miyazaki et al. |
| 4,873,965 A | 10/1989 | Danieli |
| 4,884,133 A | 11/1989 | Kanno et al. |
| 4,899,732 A | 2/1990 | Cohen |
| 4,905,667 A | 3/1990 | Foerster et al. |
| 4,907,395 A | 3/1990 | Opie et al. |
| 4,911,148 A | 3/1990 | Sosnowski et al. |
| 4,911,564 A | 3/1990 | Baker |
| 4,926,258 A | 5/1990 | Sasaki |
| 4,947,827 A | 8/1990 | Opie et al. |
| 4,947,828 A | 8/1990 | Carpenter et al. |
| 4,979,496 A | 12/1990 | Komi |
| 4,991,565 A | 2/1991 | Takahashi et al. |
| 5,019,040 A | 5/1991 | Itaoka et al. |
| 5,025,778 A | 6/1991 | Silverstein et al. |
| 5,026,377 A | 6/1991 | Burton et al. |
| 5,050,585 A | 9/1991 | Takahashi |
| RE34,110 E | 10/1992 | Opie et al. |
| 5,159,446 A | 10/1992 | Hibino et al. |
| 5,166,787 A | 11/1992 | Irion |
| 5,178,130 A | 1/1993 | Kaiya |
| 5,187,572 A | 2/1993 | Nakamura et al. |
| 5,193,525 A | 3/1993 | Silverstein et al. |
| 5,196,928 A | 3/1993 | Karasawa et al. |
| 5,253,638 A | 10/1993 | Tamburrino et al. |
| 5,260,780 A | 11/1993 | Staudt, III |
| 5,271,381 A | 12/1993 | Ailinger et al. |
| 5,305,121 A | 4/1994 | Moll |
| 5,318,031 A | 6/1994 | Mountford et al. |
| 5,329,887 A | 7/1994 | Ailinger et al. |
| 5,337,734 A | 8/1994 | Saab |
| 5,381,784 A | 1/1995 | Adair |
| 5,398,685 A | 3/1995 | Wilk et al. |
| 5,406,938 A * | 4/1995 | Mersch et al. ............... 600/138 |
| 5,434,669 A | 7/1995 | Tabata et al. |
| 5,443,781 A | 8/1995 | Saab |
| 5,447,148 A | 9/1995 | Oneda et al. |
| 5,483,951 A | 1/1996 | Frassica et al. |
| 5,494,483 A * | 2/1996 | Adair ............................ 600/111 |
| 5,518,501 A | 5/1996 | Oneda et al. |
| 5,520,607 A | 5/1996 | Frassica et al. |
| 5,530,238 A | 6/1996 | Meulenbrugge et al. |
| 5,533,496 A | 7/1996 | De Faria-Correa et al. |
| 5,536,236 A | 7/1996 | Yabe et al. |
| 5,556,367 A | 9/1996 | Yabe et al. |
| 5,613,936 A | 3/1997 | Czarnek et al. |
| 5,614,943 A | 3/1997 | Nakamura et al. |
| 5,626,553 A | 5/1997 | Frassica et al. |
| 5,634,466 A | 6/1997 | Gruner |
| 5,653,677 A | 8/1997 | Okada et al. |
| 5,667,476 A | 9/1997 | Frassica et al. |
| 5,679,216 A | 10/1997 | Takayama et al. |
| 5,681,260 A | 10/1997 | Ueda et al. |
| 5,682,199 A | 10/1997 | Lankford |
| 5,685,822 A | 11/1997 | Harhen |
| 5,692,729 A | 12/1997 | Harhen |
| 5,696,850 A | 12/1997 | Parulski et al. |
| 5,702,348 A | 12/1997 | Harhen |
| 5,706,128 A | 1/1998 | Greenberg |
| 5,711,299 A | 1/1998 | Manwaring et al. |
| 5,722,933 A | 3/1998 | Yabe et al. |
| 5,752,912 A | 5/1998 | Takahashi et al. |
| 5,762,603 A | 6/1998 | Thompson |
| 5,817,061 A | 10/1998 | Goodwin et al. |
| 5,827,177 A | 10/1998 | Oneda et al. |
| 5,833,603 A | 11/1998 | Kovacs et al. |
| 5,843,103 A | 12/1998 | Wulfman |
| 5,843,460 A | 12/1998 | Labigne et al. |
| 5,860,914 A | 1/1999 | Chiba et al. |
| 5,876,329 A | 3/1999 | Harhen |
| 5,916,147 A | 6/1999 | Boury |
| 5,924,977 A | 7/1999 | Yabe et al. |
| 5,938,587 A | 8/1999 | Taylor et al. |
| 5,982,932 A | 11/1999 | Prokoski |
| 5,989,182 A | 11/1999 | Hori et al. |
| 5,989,224 A | 11/1999 | Exline et al. |
| 6,017,358 A | 1/2000 | Yoon |
| 6,026,323 A | 2/2000 | Skladnev et al. |
| 6,066,090 A | 5/2000 | Yoon |
| 6,099,464 A | 8/2000 | Shimizu et al. |
| 6,099,466 A | 8/2000 | Sano et al. |
| 6,099,485 A | 8/2000 | Patterson |
| 6,106,463 A | 8/2000 | Wilk |
| 6,174,280 B1 | 1/2001 | Oneda et al. |
| 6,190,330 B1 | 2/2001 | Harhen |
| 6,214,028 B1 | 4/2001 | Yoon et al. |
| 6,261,226 B1 | 7/2001 | McKenna et al. |
| 6,261,307 B1 | 7/2001 | Yoon et al. |
| 6,277,064 B1 | 8/2001 | Yoon |
| 6,296,608 B1 | 10/2001 | Daniels et al. |
| 6,301,047 B1 | 10/2001 | Hoshino et al. |
| 6,350,231 B1 | 2/2002 | Ailinger et al. |
| 6,369,855 B1 | 4/2002 | Chauvel et al. |
| 6,375,653 B1 | 4/2002 | Desai |
| 6,387,043 B1 | 5/2002 | Yoon |
| 6,433,492 B1 | 8/2002 | Buonavita |
| 6,456,684 B1 | 9/2002 | Mun et al. |
| 6,461,294 B1 | 10/2002 | Oneda et al. |
| 6,482,149 B1 | 11/2002 | Torii |
| 6,503,195 B1 | 1/2003 | Keller et al. |
| 6,527,704 B1 | 3/2003 | Chang et al. |
| 6,547,724 B1 | 4/2003 | Soble et al. |
| 6,554,767 B2 | 4/2003 | Tanaka |
| 6,564,088 B1 | 5/2003 | Soller et al. |
| 6,640,017 B1 | 10/2003 | Tsai et al. |
| 6,648,816 B2 | 11/2003 | Irion et al. |
| 6,683,716 B1 | 1/2004 | Costales |
| 6,687,010 B1 | 2/2004 | Horii et al. |
| 6,697,536 B1 | 2/2004 | Yamada |
| 6,699,180 B2 | 3/2004 | Kobayashi |
| 6,736,773 B2 * | 5/2004 | Wendlandt et al. ............ 600/173 |
| 6,748,975 B2 | 6/2004 | Hartshorne et al. |
| 6,796,939 B1 | 9/2004 | Hirata et al. |
| 6,833,871 B1 | 12/2004 | Merrill et al. |
| 6,845,190 B1 | 1/2005 | Smithwick et al. |
| 6,891,977 B2 | 5/2005 | Gallagher |
| 6,916,286 B2 | 7/2005 | Kazakevich |
| 6,928,314 B1 | 8/2005 | Johnson et al. |
| 6,929,636 B1 | 8/2005 | von Alten |
| 6,947,784 B2 | 9/2005 | Zalis |
| 6,951,536 B2 | 10/2005 | Yokoi et al. |
| 6,965,702 B2 | 11/2005 | Gallagher |
| 6,966,906 B2 | 11/2005 | Brown |
| 6,974,411 B2 | 12/2005 | Belson |
| 6,997,871 B2 | 2/2006 | Sonnenschein et al. |
| 7,004,900 B2 | 2/2006 | Wendlandt et al. |
| 7,029,435 B2 | 4/2006 | Nakao |
| 7,041,050 B1 | 5/2006 | Ronald |
| 7,095,548 B1 | 8/2006 | Cho et al. |
| 7,103,228 B2 | 9/2006 | Kraft et al. |
| 7,116,352 B2 | 10/2006 | Yaron |
| 7,173,656 B1 | 2/2007 | Dunton et al. |
| 7,228,004 B2 | 6/2007 | Gallagher et al. |
| 7,280,141 B1 | 10/2007 | Frank |
| 7,317,458 B2 | 1/2008 | Wada |
| 7,322,934 B2 | 1/2008 | Miyake et al. |
| 7,341,555 B2 | 3/2008 | Ootawara et al. |
| 7,362,911 B1 | 4/2008 | Frank |
| 7,389,892 B2 | 6/2008 | Park |
| 7,405,877 B1 | 7/2008 | Schechterman |
| 7,435,218 B2 | 10/2008 | Krattiger et al. |

| | | |
|---|---|---|
| 7,436,562 B2 | 10/2008 | Nagasawa et al. |
| 7,507,200 B2 | 3/2009 | Okada |
| 7,551,196 B2 | 6/2009 | Ono et al. |
| 7,556,599 B2 | 7/2009 | Rovegno |
| 7,561,190 B2 | 7/2009 | Deng et al. |
| 7,621,869 B2 | 11/2009 | Ratnakar |
| 7,646,520 B2 | 1/2010 | Funaki et al. |
| 7,678,043 B2 | 3/2010 | Gilad |
| 7,683,926 B2 | 3/2010 | Schechterman et al. |
| 7,749,156 B2 | 7/2010 | Ouchi |
| 7,825,964 B2 | 11/2010 | Hoshino et al. |
| 7,864,215 B2 | 1/2011 | Carlsson et al. |
| 7,910,295 B2 | 3/2011 | Hoon et al. |
| 7,927,272 B2 | 4/2011 | Bayer et al. |
| 8,009,167 B2 | 8/2011 | Dekel et al. |
| 8,064,666 B2 | 11/2011 | Bayer |
| 8,070,743 B2 | 12/2011 | Kagan et al. |
| 2001/0007468 A1 | 7/2001 | Sugimoto et al. |
| 2001/0037052 A1 | 11/2001 | Higuchi et al. |
| 2001/0051766 A1 | 12/2001 | Gazdinski |
| 2001/0056238 A1 | 12/2001 | Tsujita |
| 2002/0026188 A1 | 2/2002 | Balbierz et al. |
| 2002/0039400 A1 | 4/2002 | Kaufman et al. |
| 2002/0089584 A1 | 7/2002 | Abe |
| 2002/0095168 A1 | 7/2002 | Griego et al. |
| 2002/0099267 A1 | 7/2002 | Wendlandt et al. |
| 2002/0101546 A1 | 8/2002 | Sharp et al. |
| 2002/0110282 A1 | 8/2002 | Kraft et al. |
| 2002/0115908 A1 | 8/2002 | Farkas et al. |
| 2002/0156347 A1 | 10/2002 | Kim et al. |
| 2002/0193662 A1 | 12/2002 | Belson |
| 2003/0004399 A1 | 1/2003 | Belson |
| 2003/0011768 A1 | 1/2003 | Jung et al. |
| 2003/0032863 A1 | 2/2003 | Kazakevich |
| 2003/0040668 A1 | 2/2003 | Kaneko et al. |
| 2003/0045778 A1 * | 3/2003 | Ohline et al. .................. 600/114 |
| 2003/0065250 A1 | 4/2003 | Chiel et al. |
| 2003/0088152 A1 | 5/2003 | Takada |
| 2003/0093031 A1 | 5/2003 | Long et al. |
| 2003/0093088 A1 | 5/2003 | Long et al. |
| 2003/0103199 A1 | 6/2003 | Jung et al. |
| 2003/0105386 A1 | 6/2003 | Voloshin et al. |
| 2003/0120130 A1 | 6/2003 | Glukhovsky |
| 2003/0125630 A1 | 7/2003 | Furnish |
| 2003/0125788 A1 | 7/2003 | Long |
| 2003/0130711 A1 | 7/2003 | Pearson et al. |
| 2003/0153866 A1 | 8/2003 | Long et al. |
| 2003/0161545 A1 | 8/2003 | Gallagher |
| 2003/0167007 A1 | 9/2003 | Belson |
| 2003/0171650 A1 | 9/2003 | Tartaglia et al. |
| 2003/0176767 A1 | 9/2003 | Long et al. |
| 2003/0179302 A1 | 9/2003 | Harada et al. |
| 2003/0187326 A1 | 10/2003 | Chang |
| 2003/0195545 A1 | 10/2003 | Hermann et al. |
| 2003/0197781 A1 | 10/2003 | Sugimoto et al. |
| 2003/0197793 A1 | 10/2003 | Mitsunaga et al. |
| 2003/0225433 A1 | 12/2003 | Nakao |
| 2003/0233115 A1 | 12/2003 | Eversull et al. |
| 2004/0023397 A1 | 2/2004 | Vig et al. |
| 2004/0034278 A1 | 2/2004 | Adams |
| 2004/0049096 A1 | 3/2004 | Adams |
| 2004/0059191 A1 | 3/2004 | Krupa et al. |
| 2004/0080613 A1 | 4/2004 | Moriyama |
| 2004/0097790 A1 | 5/2004 | Farkas et al. |
| 2004/0109164 A1 | 6/2004 | Horii et al. |
| 2004/0111019 A1 | 6/2004 | Long |
| 2004/0122291 A1 | 6/2004 | Takahashi |
| 2004/0141054 A1 | 7/2004 | Mochida et al. |
| 2004/0158124 A1 | 8/2004 | Okada |
| 2004/0207618 A1 | 10/2004 | Williams et al. |
| 2004/0242987 A1 | 12/2004 | Liew et al. |
| 2005/0010084 A1 | 1/2005 | Tsai |
| 2005/0014996 A1 | 1/2005 | Konomura et al. |
| 2005/0020918 A1 | 1/2005 | Wilk et al. |
| 2005/0020926 A1 | 1/2005 | Wiklof et al. |
| 2005/0038317 A1 | 2/2005 | Ratnakar |
| 2005/0038319 A1 | 2/2005 | Goldwasser et al. |
| 2005/0068431 A1 | 3/2005 | Mori |
| 2005/0085693 A1 | 4/2005 | Belson et al. |
| 2005/0085790 A1 | 4/2005 | Guest et al. |
| 2005/0096502 A1 | 5/2005 | Khalili |
| 2005/0154278 A1 | 7/2005 | Cabiri et al. |
| 2005/0165272 A1 | 7/2005 | Okada et al. |
| 2005/0165279 A1 | 7/2005 | Adler et al. |
| 2005/0177024 A1 | 8/2005 | Mackin |
| 2005/0203420 A1 | 9/2005 | Kleen et al. |
| 2005/0215911 A1 | 9/2005 | Alfano et al. |
| 2005/0222500 A1 | 10/2005 | Itoi |
| 2005/0228224 A1 | 10/2005 | Okada et al. |
| 2005/0267361 A1 | 12/2005 | Younker et al. |
| 2005/0272975 A1 | 12/2005 | McWeeney et al. |
| 2005/0272977 A1 | 12/2005 | Saadat et al. |
| 2006/0044267 A1 | 3/2006 | Xie et al. |
| 2006/0052709 A1 | 3/2006 | DeBaryshe et al. |
| 2006/0058584 A1 | 3/2006 | Hirata |
| 2006/0106286 A1 | 5/2006 | Wendlandt et al. |
| 2006/0149127 A1 | 7/2006 | Seddiqui et al. |
| 2006/0149129 A1 | 7/2006 | Watts et al. |
| 2006/0183975 A1 | 8/2006 | Saadat et al. |
| 2006/0217594 A1 | 9/2006 | Ferguson |
| 2006/0279632 A1 | 12/2006 | Anderson |
| 2006/0285766 A1 | 12/2006 | Ali |
| 2006/0293562 A1 | 12/2006 | Uchimura et al. |
| 2007/0015967 A1 | 1/2007 | Boulais et al. |
| 2007/0015989 A1 | 1/2007 | Desai et al. |
| 2007/0083081 A1 | 4/2007 | Schlagenhauf et al. |
| 2007/0103460 A1 | 5/2007 | Zhang et al. |
| 2007/0142711 A1 | 6/2007 | Bayer et al. |
| 2007/0173686 A1 | 7/2007 | Lin et al. |
| 2007/0177009 A1 | 8/2007 | Bayer et al. |
| 2007/0183685 A1 | 8/2007 | Wada et al. |
| 2007/0185384 A1 | 8/2007 | Bayer et al. |
| 2007/0225552 A1 | 9/2007 | Segawa et al. |
| 2007/0225734 A1 | 9/2007 | Bell et al. |
| 2007/0238927 A1 | 10/2007 | Ueno et al. |
| 2007/0244354 A1 | 10/2007 | Bayer |
| 2007/0270642 A1 | 11/2007 | Bayer et al. |
| 2007/0279486 A1 | 12/2007 | Bayer et al. |
| 2007/0280669 A1 | 12/2007 | Karim |
| 2007/0293720 A1 | 12/2007 | Bayer |
| 2008/0021269 A1 | 1/2008 | Tinkham et al. |
| 2008/0021274 A1 | 1/2008 | Bayer et al. |
| 2008/0033450 A1 | 2/2008 | Bayer et al. |
| 2008/0039693 A1 | 2/2008 | Karasawa |
| 2008/0064931 A1 | 3/2008 | Schena et al. |
| 2008/0065110 A1 | 3/2008 | Duval et al. |
| 2008/0071291 A1 | 3/2008 | Duval et al. |
| 2008/0079827 A1 | 4/2008 | Hoshino et al. |
| 2008/0084478 A1 | 4/2008 | Gilad et al. |
| 2008/0097292 A1 | 4/2008 | Cabiri et al. |
| 2008/0114288 A1 | 5/2008 | Whayne et al. |
| 2008/0130108 A1 | 6/2008 | Bayer et al. |
| 2008/0154288 A1 | 6/2008 | Belson |
| 2008/0199829 A1 | 8/2008 | Paley et al. |
| 2008/0200763 A1 | 8/2008 | Ueno |
| 2008/0275298 A1 | 11/2008 | Ratnakar |
| 2009/0015842 A1 | 1/2009 | Leitgeb et al. |
| 2009/0023998 A1 | 1/2009 | Ratnakar |
| 2009/0036739 A1 | 2/2009 | Hadani |
| 2009/0049627 A1 | 2/2009 | Kritzler |
| 2009/0082629 A1 | 3/2009 | Dotan et al. |
| 2009/0105538 A1 | 4/2009 | Van Dam et al. |
| 2009/0137867 A1 | 5/2009 | Goto |
| 2009/0213211 A1 | 8/2009 | Bayer et al. |
| 2009/0231419 A1 | 9/2009 | Bayer |
| 2010/0217076 A1 | 8/2010 | Ratnakar |
| 2011/0160535 A1 | 6/2011 | Bayer et al. |
| 2011/0213206 A1 | 9/2011 | Boutillette et al. |

FOREIGN PATENT DOCUMENTS

| | | |
|---|---|---|
| CN | 1628603 A | 6/2005 |
| DE | 196 26433 | 1/1998 |
| DE | 20 2006 017 173 U1 | 3/2007 |
| EP | 0 586 162 | 3/1994 |
| EP | 1 570 778 A1 | 9/2005 |
| EP | 1 769 720 A1 | 4/2007 |
| FR | 711 949 | 9/1931 |
| JP | 49-130235 A | 12/1974 |

| | | |
|---|---|---|
| JP | 56-9712 | 1/1981 |
| JP | 56-56486 A | 5/1981 |
| JP | 60-76714 A | 5/1981 |
| JP | 60-83636 A | 5/1985 |
| JP | 60-111217 A | 6/1985 |
| JP | 62-094312 U1 | 6/1987 |
| JP | 63-309912 A | 12/1988 |
| JP | 1-267514 A | 10/1989 |
| JP | 1-172847 U | 12/1989 |
| JP | 2-295530 A | 12/1990 |
| JP | 3-159629 A | 7/1991 |
| JP | 5-285091 A | 11/1993 |
| JP | 5-307144 A | 11/1993 |
| JP | 5-341210 A | 12/1993 |
| JP | 6-130308 A | 5/1994 |
| JP | 6-169880 A | 6/1994 |
| JP | 7-352 A | 1/1995 |
| JP | 7-354 A | 1/1995 |
| JP | 7-021001 U | 4/1995 |
| JP | 8-206061 A | 8/1996 |
| JP | 7-136108 A | 5/1998 |
| JP | 11-76150 A | 3/1999 |
| JP | 2003-220023 A | 8/2003 |
| JP | 2004-202252 A | 7/2004 |
| JP | 2004-525717 A | 8/2004 |
| JP | 2004-537362 A | 12/2004 |
| JP | 2007-143580 A | 6/2007 |
| JP | 4-500768 B2 | 7/2010 |
| WO | WO 93/15648 | 8/1993 |
| WO | WO-93/15648 A1 | 8/1993 |
| WO | WO-99/17542 A1 | 4/1999 |
| WO | WO-99/30506 A1 | 6/1999 |
| WO | WO 02/085194 | 10/2002 |
| WO | WO-02/094105 A2 | 11/2002 |
| WO | WO-02/094105 A3 | 11/2002 |
| WO | WO-03/013349 A2 | 2/2003 |
| WO | WO-03/013349 A3 | 2/2003 |
| WO | WO-2006/073676 A1 | 7/2006 |
| WO | WO-2006/073725 A1 | 7/2006 |
| WO | WO-2006/110275 A2 | 10/2006 |
| WO | WO-2006/110275 A3 | 10/2006 |
| WO | WO-2007/015241 A2 | 2/2007 |
| WO | WO-2007/015241 A3 | 2/2007 |
| WO | WO-2007/070644 A2 | 6/2007 |
| WO | WO-2007/070644 A3 | 6/2007 |
| WO | WO-2007/087421 A2 | 8/2007 |
| WO | WO-2007/087421 A3 | 8/2007 |
| WO | WO-2007/092533 A2 | 8/2007 |
| WO | WO-2007/092533 A3 | 8/2007 |
| WO | WO-2007/092636 A2 | 8/2007 |
| WO | WO-2007/092636 A3 | 8/2007 |
| WO | WO-2007/136859 A2 | 11/2007 |
| WO | WO-2007/136859 A3 | 11/2007 |
| WO | WO-2007/136879 A2 | 11/2007 |
| WO | WO-2007/136879 A3 | 11/2007 |
| WO | WO-2007/136879 B1 | 11/2007 |
| WO | WO-2009/014895 A1 | 1/2009 |
| WO | WO-2009/015396 A2 | 1/2009 |
| WO | WO-2009/015396 A3 | 1/2009 |
| WO | WO-2009/049322 A2 | 4/2009 |
| WO | WO-2009/049322 A3 | 4/2009 |
| WO | WO-2009/062179 A1 | 5/2009 |

OTHER PUBLICATIONS

Advisory Action mailed on May 23, 2011, for U.S. Appl. No. 11/751,605, filed May 21, 2007, 3 pages.
Amendment in Response to Non-Final Office Action filed on Jun. 29, 2009, for U.S. Appl. No. 11/215,660, filed Aug. 29, 2005, 9 pages.
Amendment in Response to Final Office Action filed on Mar. 8, 2010, for U.S. Appl. No. 11/215,660, filed Aug. 29, 2005, 11 pages.
Amendment in Response to Non-Final Office Action filed on Jun. 25, 2010, for U.S. Appl. No. 11/609,838, filed Dec. 12, 2006, 14 pages.
Amendment in Response to Non-Final Office Action filed on Aug. 30, 2010, for U.S. Appl. No. 11/215,660, filed Aug. 29, 2005, 17 pages.
Amendment in Response to Final Office Action filed on Oct. 22, 2010, for U.S. Appl. No. 11/609,838, filed Dec. 12, 2006, 15 pages.
Amendment in Response to Non-Final Office Action filed on Oct. 22, 2010, for U.S. Appl. No. 11/834,540, filed Aug. 6, 2007, 13 pages.
Amendment in Response to Non-Final Office Action filed on Feb. 9, 2011, for U.S. Appl. No. 11/828,835, filed Jul. 26, 2007, 10 pages.
Amendment in Response to Non-Final Office Action filed on Feb. 25, 2011, for U.S. Appl. No. 11/751,605, filed May 21, 2007, 15 pages.
Amendment in Response to Final Office Action filed on Feb. 28, 2011, for U.S. Appl. No. 11/215,660, filed Aug. 29, 2005, 11 pages.
Amendment in Response to Non-Final Office Action filed on Apr. 12, 2011, for U.S. Appl. No. 11/626,189, filed Jan. 23, 2007, 18 pages.
Amendment in Response to Non-Final Office Action filed on May 17, 2011, for U.S. Appl. No. 11/609,838, filed Dec. 12, 2006, 18 pages.
Amendment in Response to Final Office Action filed on May 17, 2011, for U.S. Appl. No. 11/751,605, filed May 21, 2007, 10 pages.
Amendment in Response to Final Office Action filed on May 24, 2011, for U.S. Appl. No. 11/828,835, filed Jul. 26, 2007, 13 pages.
Amendment in response to Final Office Action filed on Jun. 7, 2011, for U.S. Appl. No. 11/751,605, filed May 21, 2007, 11 pages.
European Communication mailed on Jan. 22, 2009, for European Application No. 07777255.6, filed on May 21, 2007, 2 pages.
European Office Action mailed on May 5, 2009, for European Patent Application No. 07763368.3, filed on Feb. 6, 2007, 3 pages.
European Office Action mailed on Feb. 5, 2010, for European Patent Application No. 06845440.4, filed on Dec. 13, 2006, 4 pages.
European Office Action mailed on Apr. 1, 2010, for European Patent Application No. 07717235.1, filed on Feb. 9, 2007, 2 pages.
European Office Action mailed on Nov. 8, 2010, for European Patent Application No. 05854262.2, filed on Dec. 8, 2005, 5 pages.
European Office Action mailed on Jun. 14, 2011, for European Patent Application No. 07795177.0, filed on May 21, 2007, 6 pages.
Final Office Action mailed on Aug. 23, 2010, for U.S. Appl. No. 11/609,838, filed Dec. 12, 2006, 20 pages.
Final Office Action mailed on Oct. 8, 2009, for U.S. Appl. No. 11/215,660, filed Aug. 29, 2005, 12 pages.
Final Office Action mailed on Mar. 22, 2011, for U.S. Appl. No. 11/828,835, filed Jul. 26, 2007, 11 pages.
Final Office Action mailed on Apr. 29, 2011, for U.S. Appl. No. 11/751,605, filed May 21, 2007, 9 pages.
Final Office Action mailed on Nov. 1, 2010, for U.S. Appl. No. 11/215,660, filed Aug. 29, 2005, 12 pages.
International Search Report mailed on May 18, 2006, for PCT Patent Application No. PCT/US2005/045499, filed on Dec. 8, 2005, 4 pages.
International Search Report mailed on Sep. 28, 2007, for PCT Patent Application No. PCT/US2007/002096 filed on Jan. 23, 2007, 4 pages.
International Search Report mailed on Oct. 25, 2007, for PCT Patent Application No. PCT/US2007/003322, filed on Feb. 6, 2007, 5 pages.
International Search Report mailed on Oct. 26, 2007, for PCT Patent Application No. PCT/US2007/003631, filed on Feb. 9, 2007, 5 pages.
International Search Report mailed on Dec. 11, 2007, for PCT Patent Application No. PCT/US2007/012358, filed on May 21, 2007, 3 pages.
International Search Report mailed on Jan. 28, 2008, for PCT Patent Application No. PCT/US2007/012189, filed on May 21, 2007, 2 pages.
International Search Report mailed on Oct. 23, 2008, for PCT Patent Application No. PCT/US2008/069435, filed on Jul. 8, 2008, 4 pages.
International Search Report mailed on Mar. 13, 2009, for PCT Patent Application No. PCT/US2008/083034, filed on Nov. 10, 2008, 3 pages.
International Search Report mailed on Feb. 25, 2009, for PCT Patent Application No. PCT/US2008/071390, filed on Jul. 28, 2008, 2 pages.
International Search Report mailed on Mar. 13, 2009, for PCT Patent Application No. PCT/US2008/079891, filed on Nov. 10, 2008, 2 pages.
International Search Report mailed on Apr. 6, 2009, for PCT Patent Application No. PCT/US2008/079878, filed on Oct. 14, 2008, 3 pages.
Invitation to Pay Additional Fees mailed on Dec. 29, 2008, for PCT Patent Application No. PCT/US2008/079891, filed on Oct. 14, 2008, 7 pages.

Japanese Office Action mailed on Jul. 19, 2011, for Japanese Patent Application No. 2007-550378, filed on Dec. 8, 2005, with English Translation, 11 pages.
Non-Final Office Action mailed on Mar. 25, 2009, for U.S. Appl. No. 11/215,660, filed Aug. 29, 2005, 11 pages.
Non-Final Office Action mailed on Mar. 29, 2010, for U.S. Appl. No. 11/215,660, filed Aug. 29, 2005, 16 pages.
Non-Final Office Action mailed on Apr. 6, 2010, for U.S. Appl. No. 11/609,838, filed Dec. 12, 2006, 25 pages.
Non-Final Office Action mailed on Aug. 24, 2010, for U.S. Appl. No. 11/834,540, filed Aug. 6, 2007, 11 pages.
Non-Final Office Action mailed on Oct. 18, 2010, for U.S. Appl. No. 11/626,189, filed Jan. 23, 2007, 11 pages.
Non-Final Office Action mailed on Oct. 28, 2010, for U.S. Appl. No. 11/828,835, filed Jul. 26, 2007, 11 pages.
Non-Final Office Action mailed on Dec. 22, 2010, for U.S. Appl. No. 11/751,605, filed May 21, 2007, 10 pages.
Non-Final Office Action mailed on Feb. 17, 2011, for U.S. Appl. No. 11/609,838, filed Dec. 12, 2006, 24 pages.
Non-Final Office Action mailed on Jun. 28, 2011, for U.S. Appl. No. 11/938,256, filed Nov. 10, 2007, 23 pages.
Non-Final Office Action mailed on Aug. 4, 2011, for U.S. Appl. No. 11/609,838, filed Dec. 12, 2006, 16 pages.
Non-Final Office Action mailed on Aug. 15, 2011, for U.S. Appl. No. 11/626,189, filed Jan. 23, 2007, 13 pages.
Non-Final Office Action mailed on Aug. 18, 2011, for U.S. Appl. No. 11/751,597, filed May 21, 2007, 25 pages.
Non-Final Office Action mailed on Sep. 9, 2011, for U.S. Appl. No. 11/751,596, filed May 21, 2007, 6 pages.
Non-Final Office Action mailed on Oct. 26, 2011, for U.S. Appl. No. 11/673,470, filed Feb. 9, 2007, 40 pages.
Notice of Allowance mailed on Dec. 13, 2010, for U.S. Appl. No. 11/834,540, filed Aug. 6, 2007, 4 pages.
Response to European Communication filed Feb. 6, 2009, for European Patent Application No. 07777255.6, filed on May 21, 2007, 5 pages.
Response to European Office Action filed on Nov. 11, 2009, for European Patent Application No. 07783368.3, filed on Feb. 6, 2007, 12 pages.
Response to European Office Action filed on Jul. 7, 2010, for European Patent Application No. 06845440.4, filed on Dec. 13, 2006, 13 pages.
Response to European Office Action filed on Aug. 18, 2010, for European Patent Application No. 07717235.1, filed on Feb. 9, 2007, 7 pages.
Response to European Office Action filed on Mar. 8, 2011, for European Patent Application No. 05854262.2, filed on Dec. 8, 2005, 11 pages.
Response to Restriction Requirement filed on Jan. 26, 2009, for U.S. Appl. No. 11/215,660, filed Aug. 29, 2005, 2 pages.
Response to Restriction Requirement filed on Jul. 23, 2010, for U.S. Appl. No. 11/751,605, filed May 21, 2007, 9 pages.
Response to Restriction Requirement filed on Aug. 4, 2010, for U.S. Appl. No. 11/834,540, filed Aug. 6, 2007, 5 pages.
Response to Restriction Requirement filed on Sep. 9, 2010, for U.S. Appl. No. 11/626,189, filed Jan. 23, 2007, 8 pages.
Response to Restriction Requirement filed on Oct. 21, 2010, for U.S. Appl. No. 11/828,835, filed Jul. 26, 2007, 7 pages.
Response to Restriction Requirement filed on Jun. 16, 2011, for U.S. Appl. No. 11/751,596, filed May 21, 2007, 8 pages.
Restriction Requirement mailed on Oct. 30, 2008, for U.S. Appl. No. 11/215,660, filed Aug. 29, 2005, 7 pages.
Restriction Requirement mailed on Jun. 25, 2010, for U.S. Appl. No. 11/751,605, filed May 21, 2007, 9 pages.
Restriction Requirement mailed on Jul. 13, 2010, for U.S. Appl. No. 11/834,540, filed Aug. 6, 2007, 8 pages.
Restriction Requirement mailed on Aug. 10, 2010, for U.S. Appl. No. 11/626,189, filed Jan. 23, 2007, 5 pages.
Restriction Requirement mailed on Sep. 21, 2010, for U.S. Appl. No. 11/828,835, filed Jul. 26, 2007, 6 pages.
Restriction Requirement mailed on Jun. 6, 2011, for U.S. Appl. No. 11/751,596, filed May 21, 2007, 6 pages.
Written Opinion of the International Searching Authority mailed on May 18, 2006, for PCT Patent Application No. PCT/US2005/045499, filed on Dec. 8, 2005, 9 pages.
Written Opinion of the International Searching Authority mailed on May 19, 2006, for PCT Patent Application No. PCT/US2005/044624, filed on Dec. 8, 2005, 8 pages.
Written Opinion of the International Searching Authority mailed on Jun. 20, 2007, for PCT Patent Application No. PCT/US2006/047748, filed on Dec. 13, 2006, 7 pages.
Written Opinion of the International Searching Authority mailed on Sep. 28, 2007, for PCT Patent Application No. PCT/US2007/002096 filed on Jan. 23, 2007, 8 pages.
Written Opinion of the International Searching Authority mailed on Oct. 25, 2007, for PCT Patent Application No. PCT/US2007/003322, filed on Feb. 6, 2007, 9 pages.
Written Opinion of the International Searching Authority mailed on Oct. 26, 2007, for PCT Patent Application No. PCT/US2007/003631, filed on Feb. 9, 2007, 7 pages.
Written Opinion of the International Searching Authority mailed on Dec. 11, 2007, for PCT Patent Application No. PCT/US2007/012358, filed on May 21, 2007, 6 pages.
Written Opinion of the International Searching Authority mailed on Jan. 28, 2008, for PCT Patent Application No, PCT/US2007/012189, filed on May 21, 2007, 7 pages.
Written Opinion of the International Searching Authority mailed on Oct. 23, 2008, for PCT Patent Application No. PCT/US2008/069435, filed on Jul. 8, 2008, 6 pages.
Written Opinion of the International Searching Authority mailed on Feb. 25, 2009, for PCT Patent Application No. PCT/US2008/071390, filed on Jul. 28, 2008, 7 pages.
Written Opinion of the International Searching Authority mailed on Mar. 13, 2009, for PCT Patent Application No. PCT/US2008/083034, filed on Nov. 10, 2008, 4 pages.
Written Opinion of International Searching Authority mailed on Mar. 13, 2009, for PCT Patent Application No. PCT/US2008/079891, filed on Nov. 10, 2008, 5 pages.
Written Opinion of International Searching Authority mailed on Apr. 6, 2009, for PCT Patent Application No. PCT/US2008/079878, filed on Oct. 14, 2008, 13 pages.
U.S. Appl. No. 11/828,835, filed Jun. 14, 2005, Bayer.
U.S. Appl. No. 11/834,540, filed Aug. 6, 2007, Bayer.
Invitation to Pay Additional Fees for PCT/US2007/002096, filed Jan. 23, 2007, mailed Jul. 6, 2007, 4 pgs.
Invitation to Pay Additional Fees for PCT/US2007/003631, filed Feb. 9, 2007, mailed Aug. 7, 2007, 5 pgs.
Invitation to Pay Additional Fees for PCT/US2007/003322, filed Feb. 6, 2007, mailed Aug. 7, 2007, 6 pgs.
International Search Report for PCT/US2008/069435, filed Jul. 8, 2008, mailed Oct. 23, 2008, 8 pgs.
Invitation to Pay Additional Fees for PCT/US2008/071390, filed Jul. 28, 2008, mailed Nov. 11, 2008, 5 pgs.
U.S. Appl. No. 11/153,007, filed Jun. 14, 2005, Seddiqui et al.
U.S. Appl. No. 11/160,646, filed Jul. 1, 2005, Desai et al.
U.S. Appl. No. 11/215,660, filed Aug. 29, 2005, Watts et al.
U.S. Appl. No. 11/609,838, filed Dec. 12, 2006, Bayer et al.
U.S. Appl. No. 11/626,189, filed Jan. 23, 2007, Bayer et al.
U.S. Appl. No. 11/673,470, filed Feb. 9, 2007, Bayer et al.
U.S. Appl. No. 11/736,438, filed Apr. 17, 2007, Bayer.
U.S. Appl. No. 11/751,596, filed May 21, 2007, Bayer.
U.S. Appl. No. 11/751,597, filed May 21, 2007, Bayer et al.
U.S. Appl. No. 11/751,605, filed May 21, 2007, Diel et al.
International Search Report for PCT/US2005/044624, filed Dec. 8, 2005, mailed May 19, 2006, 16 pgs.
International Search Report for PCT/US2006/047748, filed Dec. 13, 2006, mailed Jun. 20, 2007, 12 pgs.
Japanese Office Action mailed on Mar. 6, 2012, for Japanese Patent Application No. 2008-553430, filed on Feb. 6, 2007, with English Translation, 6 pages.
Extended European Search Report mailed Apr. 26, 2012, for European Patent Application No. 12153946.4, filed Feb. 3, 2012, 6 pages.
Final Office Action mailed on Apr. 23, 2012, for U.S. Appl. No. 11/938,256, filed Nov. 10, 2007, 13 pages.

Amendment in Response to Non-Final Office Action filed on May 24, 2011, for U.S. Appl. No. 11/736,438, filed Apr. 17, 2007, 11 pages.
Amendment in Response to Non-Final Office Action filed on Jun. 6, 2011, for U.S. Appl. No. 12/101,050, filed Apr. 10, 2008, 17 pages.
Amendment in Response to Final Office Action filed on Dec. 7, 2011, for U.S. Appl. No. 11/736,438, filed Apr. 17, 2007, 10 pages.
Amendment in Response to Non-Final Office Action filed on Dec. 16, 2011, for U.S. Appl. No. 11/938,256, filed Nov. 10, 2007, 10 pages.
Amendment in Response to Non-Final Office Action filed on Jan. 9, 2012, for U.S. Appl. No. 11/751,596, filed May 21, 2007, 9 pages.
Amendment in Response to Non-Final Office Action filed on Feb. 15, 2012, for U.S. Appl. No. 11/626,189, filed Jan. 23, 2007, 13 pages.
Amendment in Response to Non-Final Office Action filed on Feb. 17, 2012, for U.S. Appl. No. 11/751,597, filed May 21, 2007, 18 pages.
Final Office Action mailed on Aug. 3, 2011, for U.S. Appl. No. 11/736,438, filed Apr. 17, 2007, 11 pages.
Japanese Office Action mailed Feb. 28, 2012, for Japanese Patent Application No. 2008-545817, filed on Dec. 13, 2006, with English Translation, 6 pages.
Japanese Office Action mailed Feb. 28, 2012, for Japanese Patent Application No. 2008-551487, filed on Jan. 23, 2007, with English Translation, 9 pages.
Japanese Office Action mailed on Feb. 28, 2012, for Japanese Patent Application No. 2008-554410, filed on Feb. 9, 2007, 6 pages.
Non-Final Office Action mailed on Jan. 10, 2008, for U.S. Appl. No. 11/160,646, filed Jul. 1, 2005, 6 pages.
Non-Final Office Action mailed on Mar. 12, 2008, for U.S. Appl. No. 11/153,007, filed Jun. 14, 2005, 11 pages.
Non-Final Office Action mailed on Mar. 2, 2011, for U.S. Appl. No. 11/736,438, filed Apr. 17, 2007, 10 pages.
Non-Final Office Action mailed on May 23, 2011, for U.S. Appl. No. 12/101,050, filed Apr. 10, 2008, 11 pages.
Non-Final Office Action mailed on Oct. 21, 2011, for U.S. Appl. No. 12/251,406, filed Oct. 14, 2008, 8 pages.
Non-Final Office Action mailed on Feb. 13, 2012, for U.S. Appl. No. 13/275,206, filed Oct. 17, 2011, 13 pages.
Non-Final Office Action mailed on Feb. 14, 2012, for U.S. Appl. No. 12/251,383, filed Oct. 14, 2008, 9 pages.
Notice of Allowance mailed on Jul. 22, 2011, for U.S. Appl. No. 12/101,050, filed Apr. 10, 2008, 7 pages.
Notice of Allowance mailed on Feb. 8, 2012, for U.S. Appl. No. 11/609,838, filed Dec. 12, 2006, 8 pages.
Notice of Allowance mailed on Feb. 29, 2012, for U.S. Appl. No. 11/751,596, filed May 21, 2007, 10 pages.
Notice of Allowance mailed on Mar. 14, 2012, for U.S. Appl. No. 11/626,189, filed Jan. 23, 2007, 13 pages.
Response to European Office Action filed on Dec. 13, 2011, for European Patent Application No. 07795177.0, filed on May 21, 2007, 9 pages.
Response to Restriction Requirement filed on Feb. 8, 2011, for U.S. Appl. No. 11/736,438, filed Apr. 17, 2007, 8 pages.
Response to Restriction Requirement filed on Apr. 27, 2011, for U.S. Appl. No. 12/101,050, filed Apr. 10, 2008, 11 pages.
Restriction Requirement mailed on Dec. 10, 2010, for U.S. Appl. No. 11/736,438, filed Apr. 17, 2007, 16 pages.
Restriction Requirement mailed on Mar. 11, 2011, for U.S. Appl. No. 12/101,050, filed Apr. 10, 2008, 6 pages.
Restriction Requirement mailed on Nov. 28, 2011, for U.S. Appl. No. 12/251,383, filed Oct. 14, 2008, 6 pages.

* cited by examiner

ENDOSCOPE WITH AN IMAGING CATHETER ASSEMBLY AND METHOD OF CONFIGURING AN ENDOSCOPE

This application claims the benefit of U.S. Provisional Patent Application No. 60/771,099, filed Feb. 6, 2006, the entire disclosure of which is incorporated herein by reference.

This application is a continuation-in-part application of U.S. patent application Ser. No. 11/626,189, filed Jan. 23, 2007, the entire disclosure of which is incorporated herein by reference.

This application is a continuation-in-part application of U.S. patent application Ser. No. 11/609,838, filed Dec. 12, 2006, the entire disclosure of which is incorporated herein by reference.

This application is a continuation-in-part application of U.S. patent application Ser. No. 11/215,660, filed Aug. 29, 2005, the entire disclosure of which is incorporated herein by reference.

This application is a continuation-in-part application of U.S. patent application Ser. No. 11/030,559, filed Jan. 5, 2005, the entire disclosure of which is incorporated herein by reference.

TECHNICAL FIELD OF THE INVENTION

The present invention relates to an endoscope, an imaging catheter assembly, and a method of configuring an endoscope.

BACKGROUND OF THE INVENTION

An endoscope is a medical device comprising a flexible tube and a camera mounted on the distal end of the tube. The endoscope is insertable into an internal body cavity through a body orifice or a surgical incision to examine the body cavity and tissues for diagnosis. The tube of the endoscope has one or more longitudinal channels, through which an instrument can reach the body cavity to take samples of suspicious tissues or to perform other surgical procedures such as polypectomy.

There are many types of endoscopes, and they are named in relation to the organs or areas with which they are used. For example, gastroscopes are used for examination and treatment of the esophagus, stomach and duodenum; colonoscopes for the colon; bronchoscopes for the bronchi; laparoscopes for the peritoneal cavity; sigmoidoscopes for the rectum and the sigmoid colon; arthroscopes for joints; cystoscopes for the urinary bladder; and angioscopes for the examination of blood vessels.

Conventional endoscopes are characterized by a single forward viewing camera mounted at the distal end of the endoscope to transmit an image to an eyepiece or video display at the proximal end. The camera is used to assist a medical professional in advancing the endoscope into a body cavity and looking for abnormalities. The camera provides the medical professional with a two-dimensional view from the distal end of the endoscope. To capture an image from a different angle or in a different portion, the endoscope must be repositioned or moved back and forth. Repositioning and movement of the endoscope prolongs the procedure and causes added discomfort, complications, and risks to the patient. Additionally, in an environment such as the lower gastro-intestinal tract, flexures, tissue folds and unusual geometries of the organ may prevent the endoscope's camera from viewing all areas of the organ. The inability to view an area may cause a potentially malignant (cancerous) polyp to be missed.

This problem can be overcome by providing an auxiliary camera, which presents an image from a different point-of-view and enables viewing of areas not viewable by the endoscope's main camera. The auxiliary camera can be oriented backwards to face the main camera. This arrangement of cameras can provide both front and rear views of an area or an abnormality. In the case of polypectomy where a polyp is excised by placing a wire loop around the base of the polyp, the camera arrangement allows better placement of the wire loop to minimize damage to the adjacent healthy tissue.

SUMMARY OF THE INVENTION

In accordance with one aspect of the invention, an assembly includes a tubular body, an imaging device, and a shape memory link that connects the imaging device to the tubular body.

The shape memory link has a U-shaped natural configuration with two end segments. Preferably, one of the end segments is connected to the imaging device and the other end segment is connected to the tubular body. The end segments may be substantially parallel to each other.

The shape memory link preferably returns to its natural configuration after a force that straightens the shape memory link is removed.

The imaging device may have a cylindrical housing having first and second ends and an imaging unit disposed in the housing. The imaging unit may be disposed on the first end of the housing, and the link may be connected to the second end of the housing.

The shape memory link may include a shape memory element and flexible electrical conductors connecting electrical conductors from the imaging device to electrical conductors in the tubular body. The flexible electrical conductors preferably are a flexible PCB. The shape memory element and flexible PCB may be placed side by side in a width direction of the flexible PCB, attached to each other, or stacked to form a layered structure. The electrical conductors in the tubular body can be embedded in a wall of the tubular body or disposed in a channel of the tubular body.

The assembly may further include a light source that is placed on the link. The light source may be placed on a curved section of the link, more specifically on a concaved side of a curve section of the link. The light source can be centered in a U-shape section of the link. The light source can also be placed in a center of an S-shaped section of the link and faces away from the tubular body. Preferably, the light source faces the distal end of the tubular body. In some embodiment, the assembly may include a plurality of light sources placed on the link.

In accordance with another aspect of the invention, an endoscope assembly includes an insertion tube having an end and an imaging catheter assembly. The imaging catheter assembly may have a tubular body, a first imaging device, and a shape memory link that connects the first imaging device to the tubular body.

The endoscope assembly may include a second imaging device and a second light source, both being positioned on the end of the insertion tube. The first and second imaging devices preferably provide adjacent or overlapping viewing areas. More preferably, the first and second imaging devices provide different views of a same area. In some embodiment, the first imaging device and first light source and the second imaging device and second light source are turned on and off alternately. Preferably, the first imaging device and first light source and the second imaging device and second light source are turned on and off at a sufficiently high frequency such that eyes do not sense that they are being intermittently turned on and off.

Furthermore, each of the imaging devices may be covered by a first polarizer filter, and each of the opposing light sources may be covered by a second polarizer filter orientated at 90° relative to the opposing first polarizer filter 58. In some embodiment, only one of the imaging devices is covered by a first polarizer filter, and only the light source opposing the only one of the imaging devices is covered by a second polarizer filter orientated at 90° relative to the first polarizer filter.

In accordance with still another aspect of the invention, a method of configuring an endoscope includes the steps of straightening a U-shaped flexible shape memory link at a distal end of an imaging catheter assembly, inserting the straightened distal end of the imaging catheter assembly into a channel of an endoscope's insertion tube from a proximal end of the insertion tube; and pushing the imaging catheter assembly further into the insertion tube until an auxiliary imaging device 42 and the flexible link 44 are pushed out of the distal end of the insertion tube so that the flexible link returns to its natural bent configuration.

In accordance with yet another aspect of the invention, a minor endoscope adapted to be inserted into and through a channel of a major endoscope includes an elongated body, an imaging device located proximate to one end, and a flexible shape memory material coupled to the imaging device to the body, wherein the flexible shape memory material may be straightened for insertion into the major endoscope and wherein it assumes its original shape when it is extended beyond the major endoscope, the imaging device providing a retrograde view when the flexible shape memory material assumes its original shape.

In accordance with a further aspect of the invention, a minor endoscope adapted to be inserted into and through a channel of a major endoscope includes an elongated body, an imaging device located proximate to one end, and a channel for accessories disposed along its length.

In accordance with a still further aspect of the invention, a minor endoscope adapted to be inserted into and through a channel of a major endoscope includes an elongated body, an imaging device located proximate to one end, and a steering mechanism allowing the end minor endoscope to be turned within a dimension approximate to the diameter of the major endoscope when it is extended beyond the major endoscope, permitting the imaging device to provide a retrograde view.

In accordance with a yet further aspect of the invention, a minor endoscope to be inserted into and through a channel of a major endoscope is positioned to extend beyond the major endoscope, and permits the simultaneous imaging of a common region of the body from a substantially forward viewing angle from the major endoscope and a substantially retrograde viewing angle from the minor endoscope.

In accordance with a still yet further aspect of the invention, a minor endoscope minor endoscope to be inserted into and through a channel of a major endoscope is positioned to extend beyond the major endoscope, and permits the simultaneous imaging of a common region of the body from two different perspectives, one provided by the major endoscopes, the second provided by the minor endsocope.

In accordance with another aspect of the invention, an endoscope assembly includes an insertion tube having an end, a first imaging device mounted on the end of the insertion tube, and an imaging catheter assembly. The imaging catheter assembly preferably includes an end and a second imaging device mounted on the end of the imaging catheter assembly. The imaging catheter assembly may be partially disposed inside the insertion tube. The second imaging device may extend beyond the end of the insertion tube. The first and second imaging devices may face each other.

In accordance with another aspect of the invention, an endoscopic assembly includes an endoscope having a proximal end, a distal end, and a channel extending between the proximal and distal ends; a first imaging sensor disposed on the distal end of the endoscope, the first imaging sensor providing a forward-looking field of view; an imaging catheter assembly disposed in the channel, a distal region of the imaging catheter assembly configured to form a U-shape upon deployment beyond the distal end of the endoscope; and a second imaging sensor disposed on the distal end of the imaging catheter assembly, the second imaging sensor providing a rearward-looking field of view.

In some embodiments, the imaging catheter assembly is manufactured from a shape-memory alloy causing the imaging catheter assembly to configure from a substantially elongated shape to the U-shape upon deployment beyond the distal end of the endoscope. In still other embodiments, the forward-looking field of view and the rearward looking field of view have adjacent or overlapping edges.

BRIEF DESCRIPTION OF THE DRAWINGS

FIG. 5 shows an exploded perspective view of the link belonging to the imaging catheter assembly of FIG. 2.

DETAILED DESCRIPTION OF EMBODIMENTS OF THE INVENTION

Figure 1:
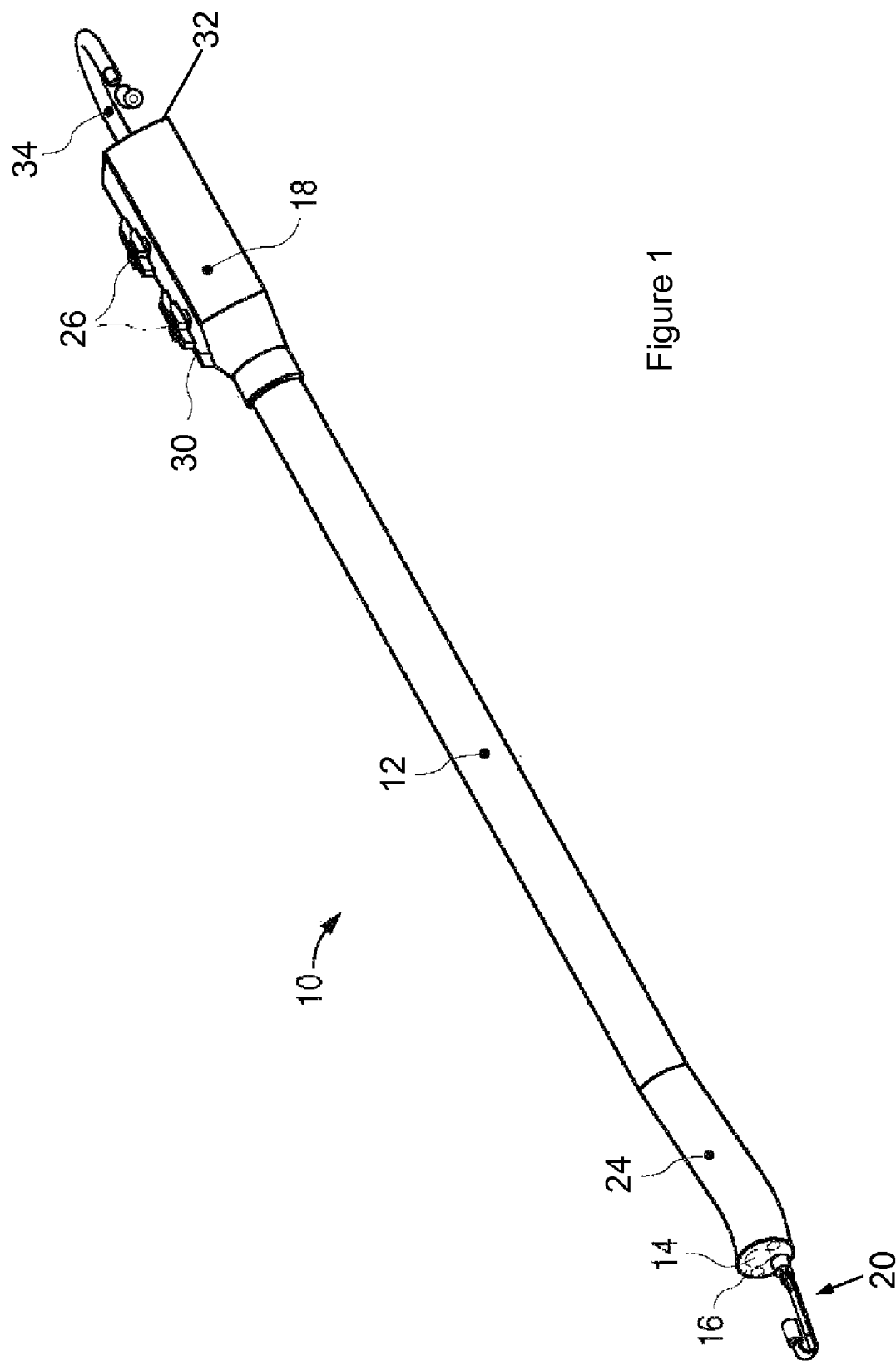
FIG. 1 shows a perspective view of an endoscope with an imaging catheter assembly according to one embodiment of the present invention.

FIG. 1 illustrates a first exemplary endoscope 10 of the present invention. This endoscope 10 can be used in a variety of medical procedures in which imaging of a body tissue, organ, cavity or lumen is required. The types of procedures include, for example, anoscopy, arthroscopy, bronchoscopy, colonoscopy, cystoscopy, EGD, laparoscopy, and sigmoidoscopy.

The endoscope 10 of FIG. 1 includes an insertion tube 12, a main imaging device 14 disposed at the distal end 16 of the insertion tube 12 (FIG. 3), a control handle 18 connected to the proximal end of the insertion tube 12, and an imaging catheter assembly 20 disposed at the distal end 16 of the insertion tube 12 and inside the insertion tube 12.

The insertion tube 12 may be detachable from the control handle 18 or may be integrally formed with the control handle 18. The diameter, length and flexibility of the insertion tube 12 depend on the procedure for which the endoscope 10 is used.

Figure 3:
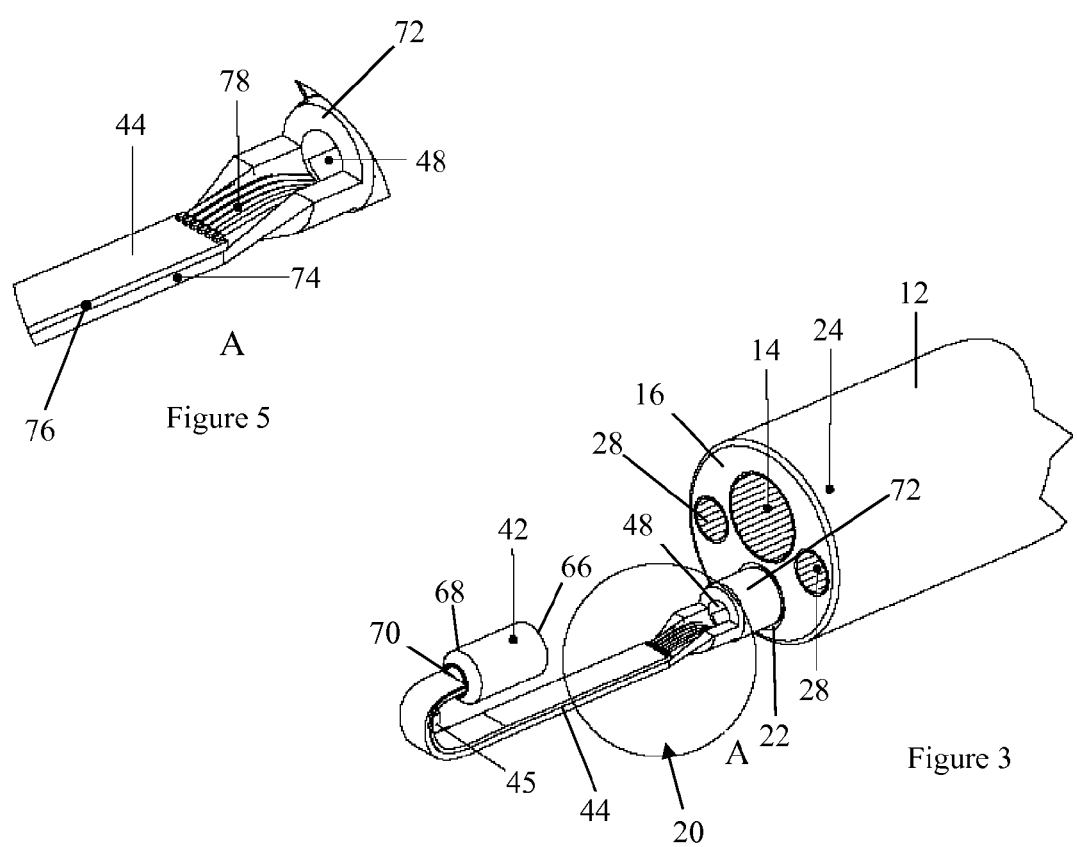
FIG. 3 shows a perspective view of the distal end of the endoscope of FIG. 1.

In the illustrated embodiment, as shown in FIG. 3, the insertion tube 12 has one longitudinal channel 22 for accommodating the imaging catheter assembly 20. In general, however, the insertion tube 12 may have more than one longitudinal channel through which an instrument can reach the body cavity to perform any desired procedures, such as to take samples of suspicious tissues or to perform other surgical procedures such as polypectomy. The instruments may be, for example, a retractable needle for drug injection, hydraulically actuated scissors, clamps, grasping tools, electrocoagulation systems, ultrasound transducers, electrical sensors, heating elements, laser mechanisms and other ablation means. In some embodiments, one of the channels can be used to supply a washing liquid such as water for washing. A cap (not shown) may be included at the opening of the washing channel to divert the washing liquid onto a lens of the main imaging device 14 for cleaning. Another or the same channel may be used to supply a gas, such as $CO_2$ or air, into the organ. The channels may also be used to extract fluids or inject fluids, such as a drug in a liquid carrier, into the body. Various biopsy, drug delivery, and other diagnostic and therapeutic devices may also be inserted via the channels to perform specific functions.

The insertion tube 12 preferably is steerable or has a steerable distal end region 24 as shown in FIG. 1. The length of the distal end region 24 may be any suitable fraction of the length of the insertion tube 12, such as one half, one third, one fourth, one sixth, one tenth, or one twentieth. The insertion tube 12 may have control cables (not shown) for the manipulation of the insertion tube 12. Preferably, the control cables are symmetrically positioned within the insertion tube 12 and extend along the length of the insertion tube 12. The control cables may be anchored at or near the distal end 16 of the insertion tube 12. Each of the control cables may be a Bowden cable, which includes a wire contained in a flexible overlying hollow tube. The wires of the Bowden cables are attached to controls 26 in the handle 18. Using the controls, the wires can be pulled to bend the distal end region 24 of the insertion tube 12 in a given direction. The Bowden cables can be used to articulate the distal end region 24 of the insertion tube 12 in different directions.

The main imaging device 14 at the distal end 16 of the insertion tube 12 may include, for example, a lens, single chip sensor, multiple chip sensor or fiber optic implemented devices. The main imaging device 14, in electrical communication with a processor and/or monitor, may provide still images or recorded or live video images. In addition to the main imaging device 14, the distal end 16 of the insertion tube 12 may include one or more light sources 28 (FIG. 3), such as light emitting diodes (LEDs) or fiber optical delivery of light from an external light source. The light sources 28 preferably are equidistant from the main imaging device 14 to provide even illumination. The intensity of each light source 28 can be adjusted to achieve optimum imaging. The circuits for the main imaging device 14 and light sources 28 may be incorporated into a printed circuit board (PCB).

The insertion tube 12 may include a flexible ribbon coil (not shown) and a flexible sheath (not shown) that is used to protect the internal components of the insertion tube 12, such as the channels, wires and cables, from the environment of the body.

Preferably, the control handle 18 has one or more ports and/or valves (not shown) for controlling access to the channels of the insertion tube 12. The ports and/or valves can be air or water valves, suction valves, instrumentation ports, and suction/instrumentation ports. As shown in FIG. 1, the control handle 18 may additionally include buttons 30 for taking pictures with the main imaging device 14, the imaging catheter assembly 20, or both.

The proximal end 32 of the control handle 18 may include an accessory outlet 34 (FIG. 1) that provides fluid communication between the air, water and suction channels and the pumps and related accessories. The same outlet or a different outlet can be used for electrical lines to light and imaging components at the distal end of the endoscope 10.

Figure 2:
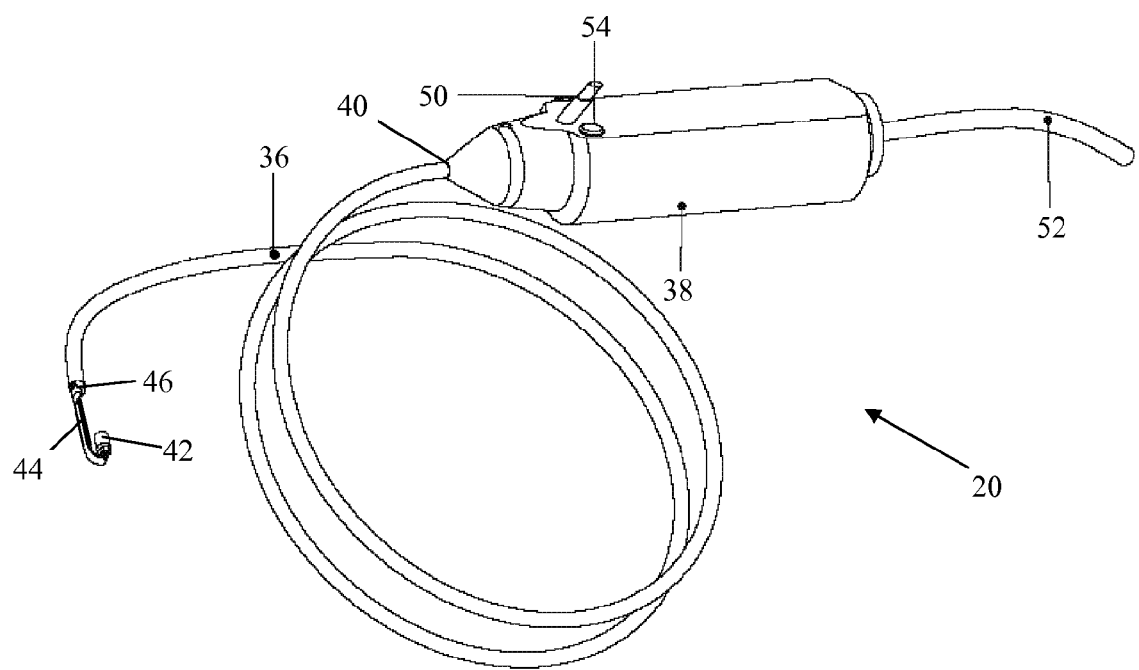
FIG. 2 shows a perspective view of the imaging catheter assembly shown in FIG. 1.

As shown in FIG. 2, the imaging catheter assembly 20 may include a tubular body 36, a handle 38 connected to the proximal end 40 of the tubular body 36, an auxiliary imaging device 42, a link 44 that provides physical and/or electrical connection between the auxiliary imaging device 42 to the distal end 46 of the tubular body 36, and a light source 45 (illustrated in FIG. 3).

The imaging catheter assembly 20 is used to provide an auxiliary imaging device at the distal end of the endoscope 10. To this end, the imaging catheter assembly 20 is placed inside the channel 22 of the endoscope's insertion tube 12 with its auxiliary imaging device 42 disposed beyond the distal end 16 of the insertion tube 12. This can be accomplished by first inserting the distal end of the imaging catheter assembly 20 into the insertion tube's channel 22 from the endoscope's handle 18 and then pushing the imaging catheter assembly 20 further into the channel 22 until the auxiliary imaging device 42 and link 44 of the imaging catheter assembly 20 are positioned outside the distal end 16 of the insertion tube 12 as shown in FIG. 3.

The tubular body 36 of the imaging catheter assembly 20 may have any suitable configuration. In terms of its length, the tubular body 36 preferably is sufficiently long such that the auxiliary imaging device 42 and link 44 can extend beyond the distal end 16 of the insertion tube 12. The preferred cross-section of the illustrated tubular body 36 is circular, although the cross-section may have any other suitable configuration, such as an elliptical or polygonal configuration.

In the illustrated embodiment, as shown in FIG. 3, the tubular body 36 has a channel 48 expanding its entire length, although the tubular body 36 generally may have no channels or two or more channels. This channel 48 may be used for various purposes. For example, the channel 48 may be used for passing instruments, such as snares or biopsy forceps, from the proximal end of the imaging catheter assembly 20 to the distal end. Each of the instruments may be incorporated into the imaging catheter assembly 20, rather than as a separate instrument. The opening for the channel 48 at the distal end may include a slope or ramp at a predetermined angle so as to guide any instruments away from the link 44 and into a predefined position and alignment so as to be within the field-of-view and focus of the imaging catheter assembly 20.

The channel 48 may also be used to control the flow of fluid into and from the body cavity. For example, the channel 48 may be used to control the flow of air into and from the body cavity (suction or insufflation) as well as to supply water to, for example, wash the auxiliary imaging device 42. The channel 48 may further be used for the routing of electrical conductors between the auxiliary imaging device 42 and the handle 38. The channel 48 can be provided with a lubricious liner to ease the movement of an instrument inside the channel 48. The lubricious liner may be made from any suitable material such as PTFE or Polyimide.

Figure 10:
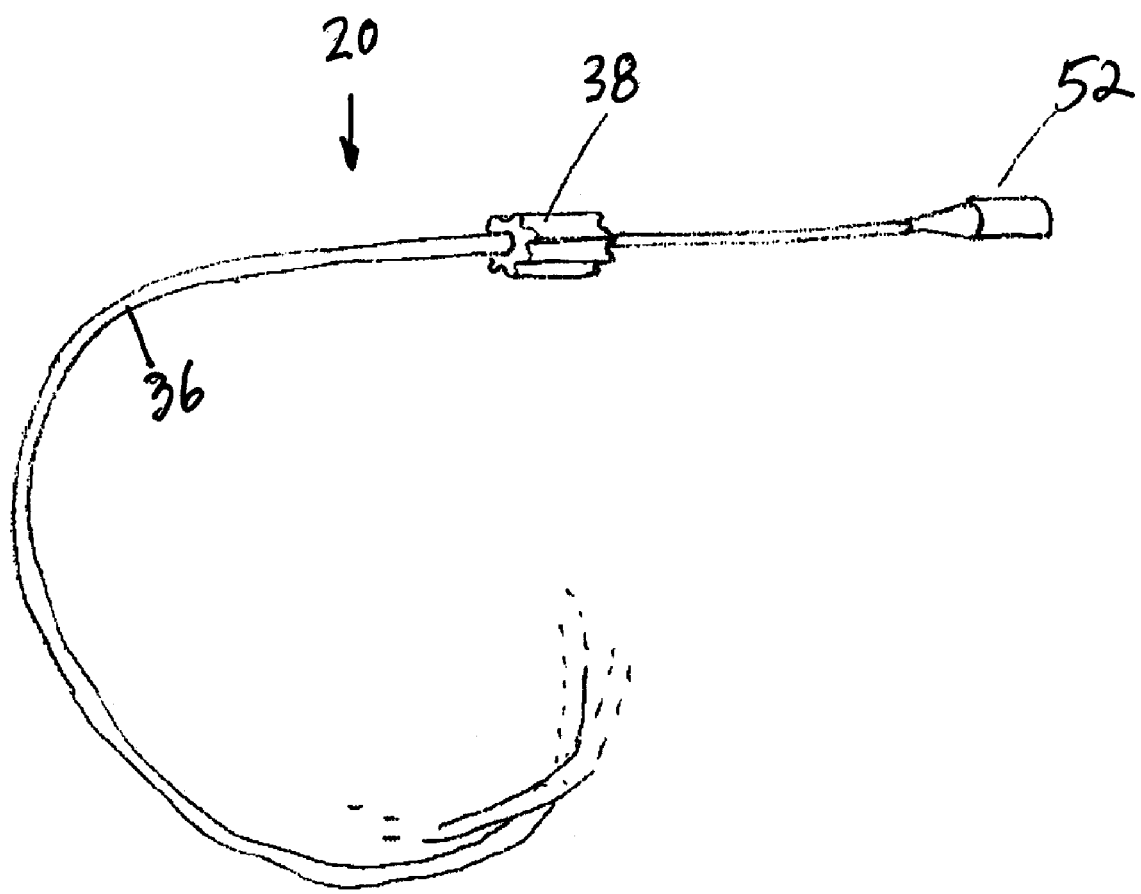
FIG. 10 shows a perspective view of an imaging catheter assembly according to a yet further embodiment of the present invention.

The handle 38 of the imaging catheter assembly 20 may control various functions of the imaging catheter assembly 20. For example, the handle 38 may serve as a convenient way to deploy and/or rotate the imaging catheter assembly 20 inside the channel 22 of the insertion tube 12. The handle 38 may also provide an access port 50 for the channel 48 of the tubular body 36. The handle 38 may additionally provide a connector 52, to which electrical conductors from the auxiliary imaging device 42 and other components of the imaging catheter assembly 20 are connected. The connector 52 can be used to connect the auxiliary imaging device 42 and other components to a device outside of the imaging catheter assembly 20, such as a control box. The handle 38 may further provide a switch 54 that is used to operate the auxiliary imaging device 42 to capture still images. Alternatively, as shown in FIG. 10, the handle 38 may be simply configured to be used to rotate the imaging catheter assembly 20.

Figure 4:
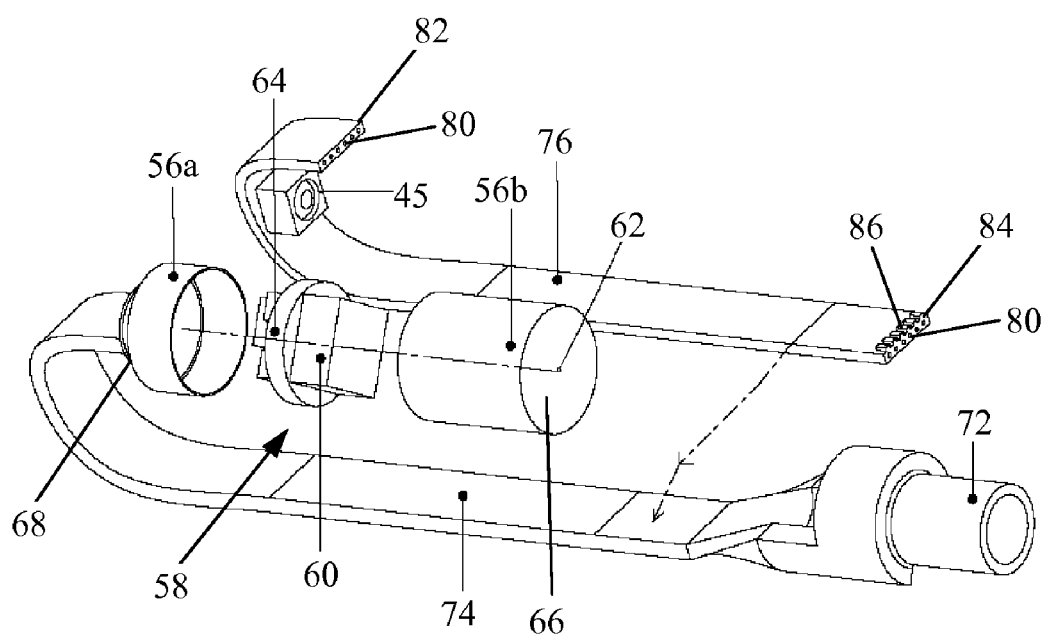
FIG. 4 shows a perspective view of a portion of a link belonging to the imaging catheter assembly shown in FIG. 2.

As shown in FIG. 4, the auxiliary imaging device 42 may include a housing 56*a*, 56*b* and an imaging unit 58 disposed in the housing 56*a*, 56*b*. In this embodiment, the housing 56*a*, 56*b* has a generally cylindrical configuration, but in general the housing may have any suitable configuration such as a spherical or cubic configuration. The housing 56*a*, 56*b* includes two parts 56*a*, 56*b* that are sealingly joined to form the housing 56*a*, 56*b*. The housing 56*a*, 56*b* may be made from any suitable material such as stainless steel or a plastic material.

As shown in FIG. 4, the imaging unit 58 may include a lens 62, an imaging sensor 60, and a printed circuit board (PCB) 64 containing electrical components of the imaging unit 58. The lens 62 is installed in an aperture on a first end 66 of the housing 56*a*, 56*b*, and may include a plurality of optical elements in a holder or barrel which focuses the incoming light from the surroundings onto a photosensitive area of the image sensor 60.

The imaging sensor 60 may be an electronic device which converts light incident on photosensitive semiconductor elements into electrical signals. The imaging sensor 60 may detect either color or black-and-white images. The signals from the imaging sensor 60 can be digitized and used to reproduce an image that is incident on the imaging sensor 60. Two commonly used types of image sensors are Charge Coupled Devices (CCD) such as a VCC-5774 produced by Sanyo of Osaka, Japan and Complementary Metal Oxide Semiconductor (CMOS) camera chips such as an OVT 6910 produced by OmniVision of Sunnyvale, Calif.

Alternatively, the imaging unit 58 may include a coherent fiber optic bundle and a lens for channeling light into the coherent fiber optic bundle, which then delivers the light from the distal end of the imaging catheter assembly 20 to an imaging sensor located at the proximal end of, or external to, the imaging catheter.

On its second end 68, the housing 56*a*, 56*b* of the auxiliary imaging device 42 may include an opening 70 (FIG. 3) for a flexible PCB 76 (FIG. 4) to pass through for connection with the imaging unit 58. The flexible PCB 76 electrically connects the imaging unit 58 to the electrical conductors 78 (FIG. 5) which extend through tubular body 36.

Figure 7:
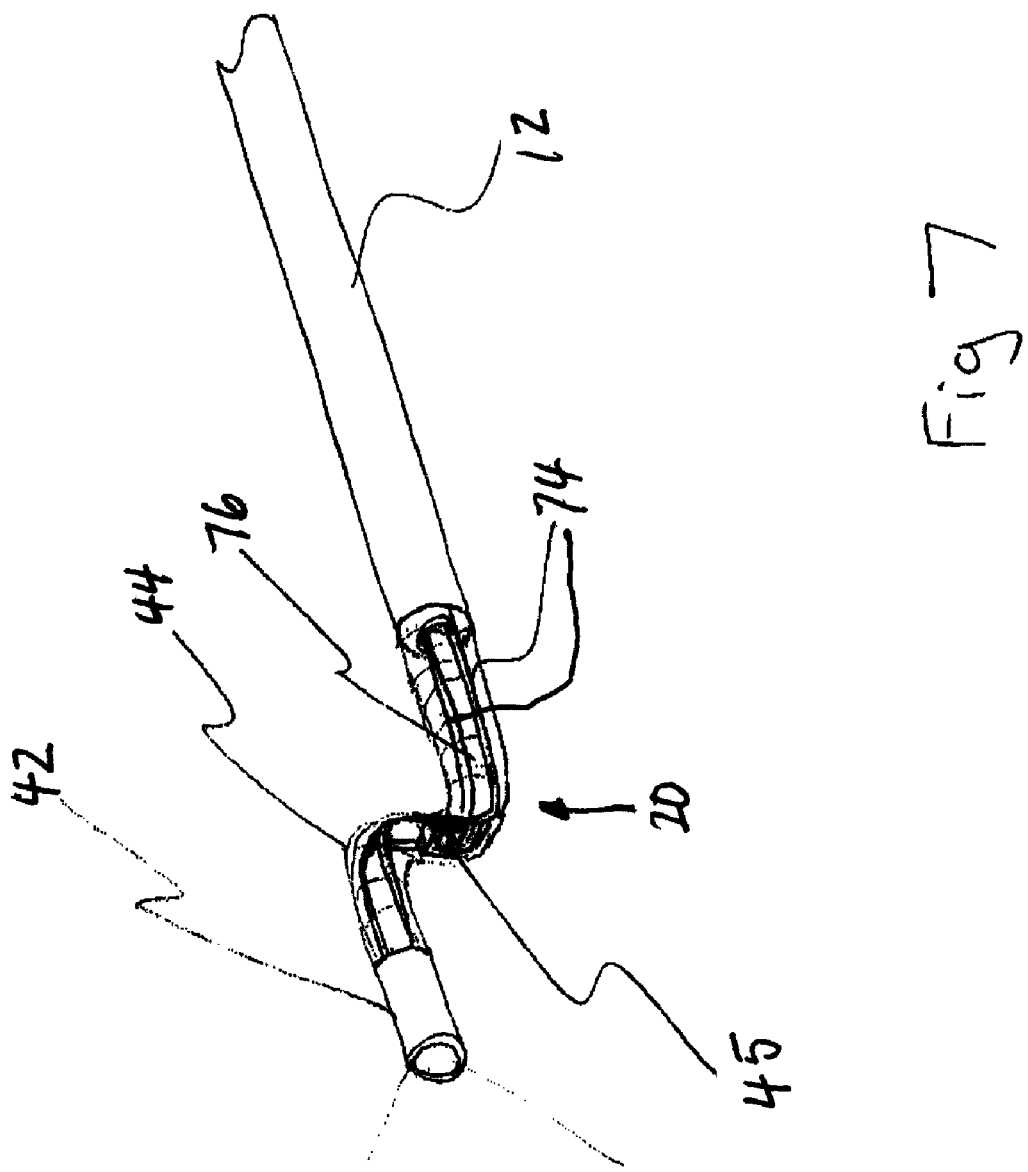
FIG. 7 shows a perspective view of an imaging catheter assembly according to still another embodiment of the present invention.

When the imaging catheter assembly 20 is properly installed in the insertion tube 12, the auxiliary imaging device 42 of the imaging catheter assembly 20 preferably faces backwards towards the main imaging device 14 as illustrated in FIG. 3. The auxiliary imaging device 42 may be oriented so that the auxiliary imaging device 42 and the main imaging device 14 have adjacent or overlapping viewing areas. Alternatively, the auxiliary imaging device 42 may be oriented so that the auxiliary imaging device 42 and the main imaging device 14 simultaneously provide different views of the same area. Preferably, the auxiliary imaging device 42 provides a retrograde view of the area, while the main imaging device 14 provides a front view of the area. However, the auxiliary imaging device 42 could be oriented in other directions to provide other views, including a forward view, as shown in FIG. 7, and views that are substantially parallel to the axis of the main imaging device 14. The light source 45 of the auxiliary imaging device may also face forward as shown in FIG. 7. Such an embodiment could be useful when the size of the imaging catheter assembly permits to reach locations that are too narrow to allow passage of the insertion tube.

As shown in FIGS. 2 and 3, the link 44 connects the auxiliary imaging device 42 to the distal end 46 of the tubular body 36. Preferably, the link 44 is a flexible link that is at least partially made from a flexible shape memory material that substantially tends to return to its original shape after deformation. Shape memory materials are well known and include shape memory alloys and shape memory polymers. A suitable flexible shape memory material is a shape memory alloy such as nitinol. The flexible link 44 is straightened to allow the distal end of the imaging catheter assembly 20 to be inserted into the proximal end of channel 22 of the insertion tube 12 and then pushed towards the distal end 16 of the insertion tube 12. When the flexible link 44 is straightened inside the channel 22 of the insertion tube 12, the first end 66 of the auxiliary imaging device 42 faces away from the tubular body 36, a direction parallel to the main imaging device 14, while the second end 68 of the auxiliary imaging device 42 faces back towards the tubular body 36 and handle 38. When the auxiliary imaging device 42 and flexible link 44 are pushed sufficiently out of the distal end 16 of the insertion tube 12, the flexible link 44 resumes its natural bent configuration as shown in FIG. 3. The natural configuration of the flexible link 44 is the configuration of the flexible link 44 when the flexible link 44 is not subject to any force or stress. When the flexible link 44 resumes its natural bent configuration, the first end 66 of the auxiliary imaging device 42 faces substantially back towards the tubular body 36 (FIG. 2) and back towards the distal end 16 of the insertion tube 12 (FIG. 3) while the second end 68 of the auxiliary imaging device 42 faces away from the tubular body 36 (FIG. 2) and away from the distal end 16 of the insertion tube 12 (FIG. 3).

The flexible link may have any suitable configuration that allows it to be straightened under force and to return to its natural bent configuration when the force is removed. For example, the flexible link may have a U-shaped, S-shaped, right angle, or ramp configuration. In the illustrated embodiment, the flexible link 44 has a U-shaped natural configuration with two end segments that are substantially parallel to each other. Preferably, the distance between the end segments is equal to or less than a diameter of the insertion tube. One of the end segments is connected to the auxiliary imaging device 42 and other end segment is connected to the tubular body 36. Although the end segment connected to the tubular body 36 is much longer in the illustrated embodiment, the end segment connected to the auxiliary imaging device 42 may be longer in other embodiments. The flexible link 44 may have a generally elongated flat configuration with a hollow tubular end 72 for connection to the tubular body 36. As shown in FIG. 4, the hollow tubular end 72 of the flexible link 44 may be attached to the distal end 46 of the tubular body 36 by concentrically mating with the channel 48 of the tubular body 36. The attachment may be accomplished by any suitable means including adhesive bonding, welding or soldering. At the other end, the flexible link 44 may be joined to the auxiliary imaging device 42 by any suitable means such as adhesive bonding, welding or soldering.

Figure 9:
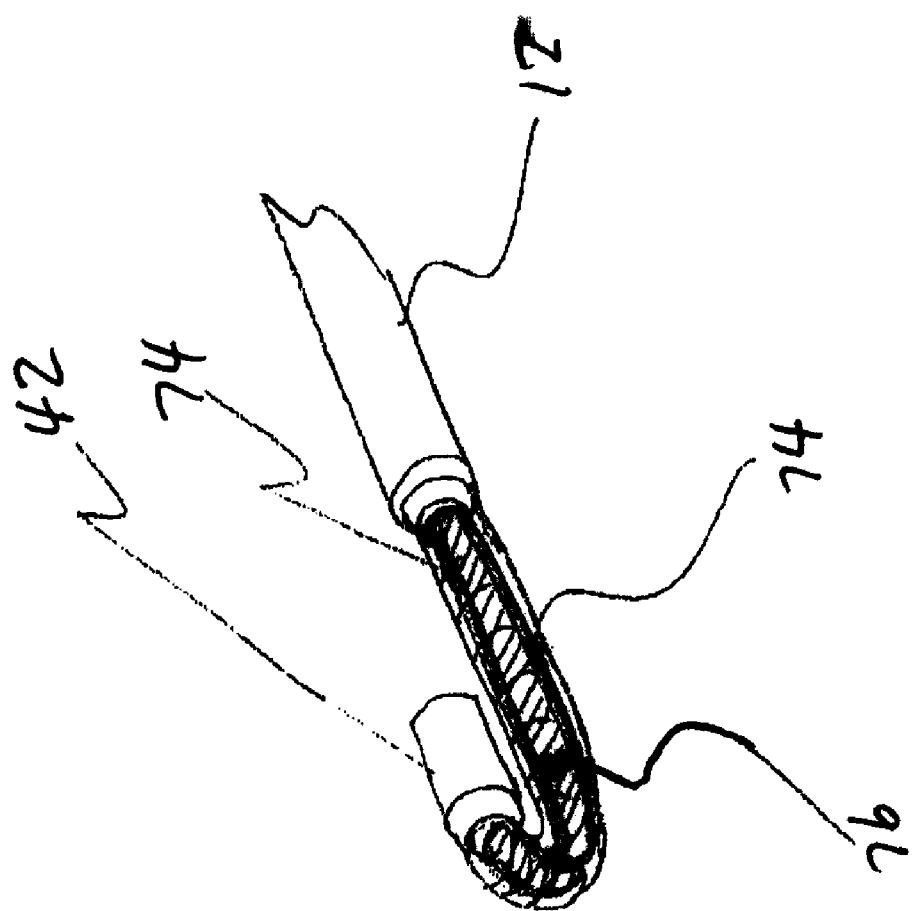
FIG. 9 shows a perspective view of an imaging catheter assembly according to a further embodiment of the present invention.

In the illustrated embodiment, as shown in FIGS. 4 and 5, the flexible link 44 may include a flexible shape memory element 74 and a flexible PCB 76 that electrically connects the auxiliary imaging device 42 to the electrical conductors 78 in the tubular body 36. The flexible shape memory element 74 preferably performs the shape memory function of the flexible link 44, and the flexible PCB 76 is attached to the flexible shape memory element 74 so that its shape changes with the shape of the flexible shape memory element 74. Alternatively, the flexible PCB 76 and flexible shape memory element 74 may be merely placed next to one another but not attached. Even when the flexible PCB 76 and flexible shape memory element 74 are not attached to each other, they will still undergo substantially the same shape changes as long as they are appropriately configured (such as if their lengths are similar). In the illustrated embodiment, the flexible shape memory element 74 and flexible PCB 76 have a similar configuration and are stacked in the thickness direction of the flexible PCB 76 to form a layered structure. In general, however, they may have different configurations and may be arranged relative to each other in any other suitable manner. For example, one of the shape memory element and flexible PCB may be wider than the other, and they may be placed side by side in the width direction of the flexible PCB 76, as shown in FIG. 9 as opposed to being stacked in the thickness direction of the flexible PCB 76. Furthermore, the shape memory element may include two components, and the flexible PCB 76 may be placed between the two components in either the thickness direction or the width direction of the flexible PCB 76. In a preferred embodiment, the components of the shape memory element may each be a wire-shaped shape memory component, and the wire-shaped components may be placed on the two width sides of the flexible PCB, respectively. This symmetrical arrangement provides a common central bending axis for both the shape memory element and the flexible PCB.

As shown in FIG. 4, the flexible PCB 76 includes electrical conductors 80 that connect the auxiliary imaging device 42 to the electrical conductors 78 in the tubular body 36. At one end 82 of the flexible PCB 76, the electrical conductors 80 of the flexible PCB 76 are connected to the auxiliary imaging device 42. At the other end 84 of the flexible PCB 76, the electrical conductors 80 of the flexible PCB 76 are connected to the electrical conductors 78 in the tubular body 36. This end 84 of the flexible PCB 76 may have pads 86 for the connection between the electrical conductors 78 and electrical conductors 80.

Figure 8:
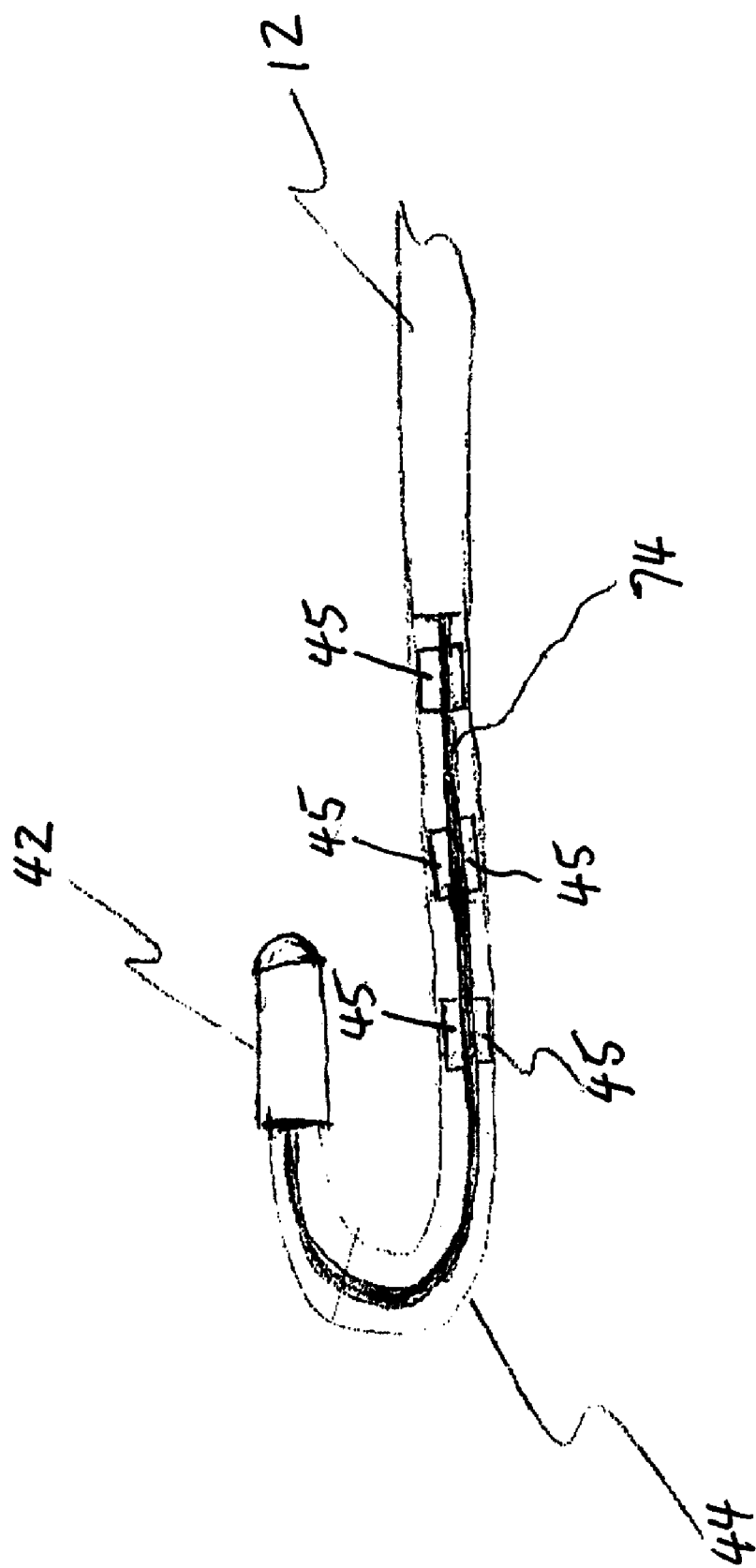
FIG. 8 shows a perspective view of an imaging catheter assembly according to yet another embodiment of the present invention.
Figure 11:
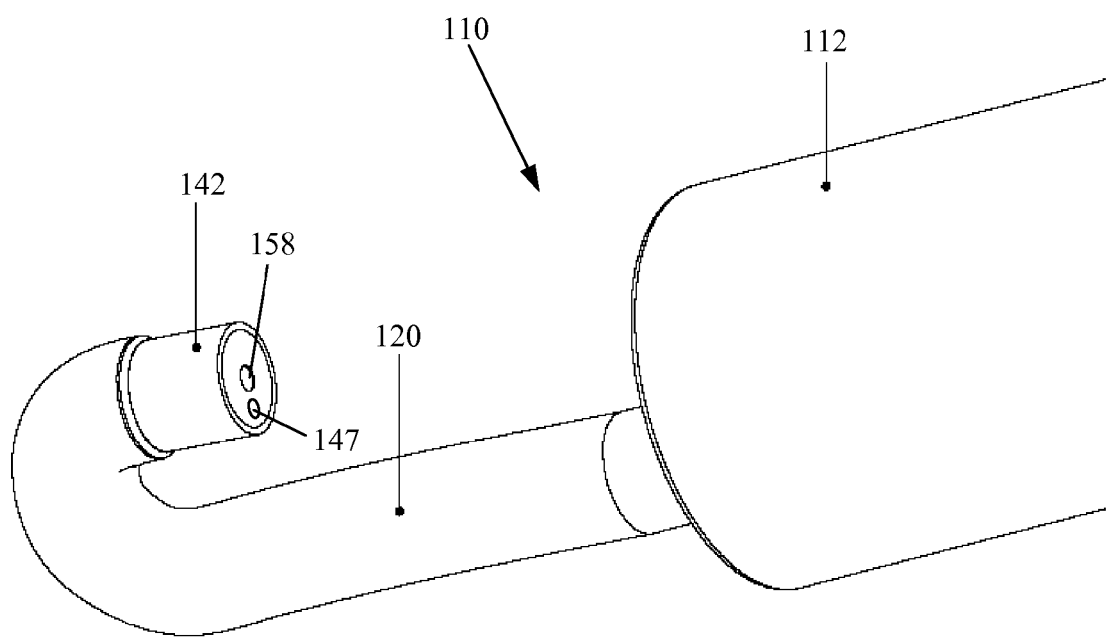
FIG. 11 shows a perspective view of an endoscope with an imaging catheter assembly according to another embodiment of the present invention.

In the illustrated embodiment, the light source 45 (as well as other components) of the imaging catheter assembly 20 is placed on the flexible link 44, in particular on the curved concave portion of the flexible link 44, although the light source 45 may be placed at any other suitable position, such as on the rear facing end of the auxiliary imaging device 42 as shown in FIG. 11. Multiple light sources 45 may be located along the flexible link 44, including along a straight portion of the flexible link 44 as shown in FIG. 8. The light sources 45 provide illumination for the auxiliary imaging device 42 and may face substantially the same direction as the auxiliary imaging device 42 as shown in FIG. 4 or perpendicular to it as shown in FIG. 8. The light sources 45 may be light emitting diodes (LEDs) soldered onto conductive pads (not shown) on the flexible PCB 76. Alternatively, fiber optic bundles may be used to deliver light from an external light source to the distal region of the imaging catheter.

The flexible link may be encapsulated or shrouded by flexible tubing, heat-shrinkable tubing, urethanes, rubber or silicon so as to allow smooth profile transition from the tubular body to the imaging device. This encapsulation may be translucent to allow light from the light source to project through the encapsulation, or the encapsulation may include a window section around each light source.

Since the main imaging device 14 and its light source 28 face the auxiliary imaging device 42 and its light source 45, the light sources 28, 45 of the imaging devices 14, 42 may interfere with the opposing imaging device 42, 14. That is, light source 28 may shine directly into auxiliary imaging device 42 and light source 45 may shine directly into main imaging device 14, degrading both images. To reduce the interference, polarizer filters may be used with the imaging devices 14, 42 and light sources 28, 45. Specifically, the main imaging device 14 and/or its light source 28 may be covered by a first set of polarizer filters of a given orientation. And the auxiliary imaging device 42 and/or its light source 45 may be covered by a second set of polarizer filters orientated at 90° relative to the first set of polarizer filters. The use of polarizer filters to reduce light interference is well known and will not be described in further detail.

As an alternative to polarizer filters, the imaging devices 14, 42 and their light sources 28, 45 may be turned on and off alternately to reduce or prevent light interference. In other words, when the main imaging device 14 and its light sources 28 are turned on, the auxiliary imaging device 42 and its light source 45 are turned off. And when the main imaging device 14 and its light sources 28 are turned off, the auxiliary imaging device 42 and its light source 45 are turned on. Preferably, the imaging devices 14, 42 and their light sources 28, 45 are turned on and off at a sufficiently high frequency that eyes do not sense that the light sources are being turned on and off.

The auxiliary imaging device 42 and its light source 45 are connected to a control box (not shown) via electrical conductors that extend from the imaging device 42 and light source 45; through the flexible PCB 76, tubular body 36, and handle 38; to the control box. The electrical conductors may carry power and control commands to the auxiliary imaging device 42 and its light source 45 and image signals from the auxiliary imaging device 42 to the control box. In the illustrated embodiment, the electrical conductors 78 in the tubular body 36 may be embedded in the wall of the tubular body 36, or simply in the tubular body if the tubular body does not have a channel, during the fabrication process or disposed in the channel 48 of the tubular body 36. The embedding of the electrical conductors in the tubular body 36 may be done by a braiding or coiling process to achieve the desired stiffness of the tubular body 36. A short length of the embedded electrical conductors may be exposed at either end of the tubular body 36 to allow connections to be made. The connections may then be sealed by means of, for example, heat-shrinking tubing, a sheath or an adhesive.

The control box includes at least an image and signal processing device and a housing in which the image and signal processing device is disposed, although the control box can be configured in any suitable manner. The housing may include a control panel and connectors. The control panel includes buttons and knobs for controlling the functionalities of the control box.

The image and signal processing device may include one or more integrated circuits and memory devices along with associated discrete components. The device allows image signals from the imaging devices 14, 42 to be processed for the enhancement of image quality, extraction of still images from the image signals, and conversion of video format for compatibility with the display device.

The control box preferably processes the video image signal from the auxiliary imaging device 42 and transmits it to a display device such as a television or a monitor such as a liquid crystal display monitor. Still images can be captured from the video image signal using the switch 54 on the handle 38 of the imaging catheter assembly 20. The video image or still image may be displayed on the display device. The display device may also include textual data that are used to display information such as patient information, reference numbers, date, and/or time.

The image signal from the main imaging device 14 may also be processed by the control box in the same way that the image signal from the auxiliary imaging device 42 is processed. The images from the main and auxiliary imaging devices 14, 42 may be displayed on two separate monitors or on the same monitor with a split screen.

The control box may further be used to adjust the parameters of the imaging devices 14, 42 and their light sources 28, 45, such as brightness, exposure time and mode settings. The adjustment can be done by writing digital commands to specific registers controlling the parameters. The registers can be addressed by their unique addresses, and digital commands can be read from and written to the registers to change the various parameters. The control box can change the register values by transmitting data commands to the registers.

The control box may additionally be used as an interface to the patient records database. A large number of medical facilities now make use of electronic medical records. During the procedure relevant video and image data may need to be recorded in the patient electronic medical records (EMR) file. The signal processing circuit can convert image and video data to a format suitable for filing in the patient EMR file such as images in jpeg, tif, or .bmp format among others. The processed signal can be transmitted to the medical professional's computer or the medical facilities server via a cable or dedicated wireless link. A switch on the control panel can be used to enable this transmission. Alternatively the data can be stored with a unique identification for the patient in electronic memory provided in the control box itself. The signal processing circuit can be utilized to convert the video and image data to be compatible with the electronic medical records system used by the medical professional. The processing may include compression of the data. A cable or a wireless link may be used to transmit the data to a computer.

During endoscopy, a physician may straighten the flexible link 44 of the imaging catheter assembly 20 and then insert the straightened distal end of the imaging catheter assembly 20 into the channel 22 of the endoscope's insertion tube 12 from the handle 18. The imaging catheter assembly 20 can then be pushed towards the distal end 16 of the insertion tube 12. When the auxiliary imaging device 42 and flexible link 44 are pushed out of the distal end 16 of the insertion tube 12, the flexible link 44 resumes its natural bent configuration as shown in FIG. 2.

The main imaging device 14 now captures a front-viewing image, and the auxiliary imaging device 42 simultaneously captures a rear-viewing image of the same area. The control box processes the video image signals and transmits them to a display device or display devices for viewing by the physician. The physician can adjust the view of the auxiliary imaging device 42 by rotating the handle 38 of the imaging catheter assembly 20 and/or by pushing or pulling the imaging catheter assembly 20 in the channel 22 of the insertion tube 12. As a result, the physician can inspect a lesion such as a cancer or polyp at various angles.

Figure 6:
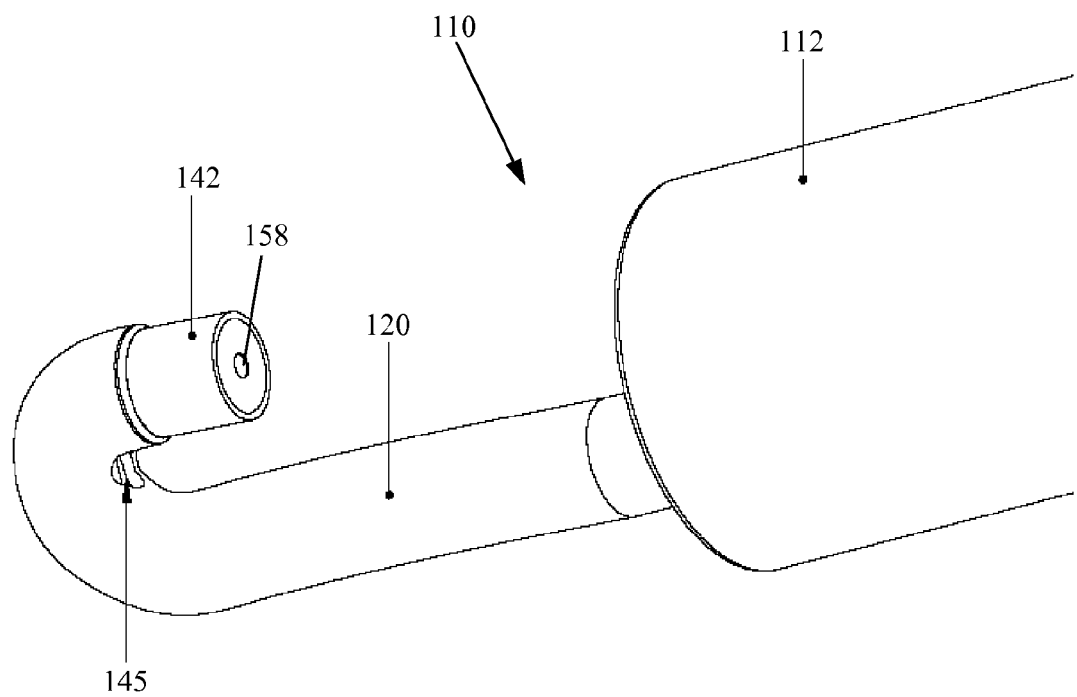
FIG. 6 shows a perspective view of an endoscope with an imaging catheter assembly according to another embodiment of the present invention.

FIG. 6 illustrates a further embodiment of the present invention. In this embodiment, the endoscope 110 has an insertion tube 112 and an imaging catheter assembly 120 positioned at the distal end of and inside the insertion tube 112. The imaging catheter assembly 120 includes an auxiliary imaging device 142 disposed at the distal end of the imaging catheter assembly 120. The auxiliary imaging device 142 includes an imaging unit 158 and a light source 145. When the imaging catheter assembly 120 is properly installed in the insertion tube 12, the auxiliary imaging device 142 of the imaging catheter assembly 20 preferably faces backwards towards the main imaging device (not shown). The auxiliary imaging device 142 may be oriented so that the auxiliary imaging device 142 and the main imaging device have adjacent or overlapping viewing areas. Alternatively, the auxiliary imaging device 142 may be oriented so that the auxiliary imaging device 142 and the main imaging device simultaneously provide different views of the same area. Preferably, the auxiliary imaging device 142 provides a retrograde view of the area, while the main imaging device provides a front view of the area. However, the auxiliary imaging device 142 could be oriented in other directions to provide other views, including views that are substantially parallel to the axis of the main imaging device.

The distal end region of the imaging catheter assembly 120 preferably is made by shape setting of the catheter assembly 120 itself. This process is widely used and understood in the art and involves a process combination of heat and fixturing to create the pre-shaped distal end. The pre-shaped distal end may be supported by a piece of a shape memory material such as nitinol set in a similar shape. The imaging catheter assembly 120 may also include a light source 145. In general, this endoscope 110 is similar to the endoscope 10 shown in FIGS. 1-5, except the distal end portion of the imaging catheter assembly 120.

FIG. 11 illustrates another embodiment that is similar to the embodiment shown in FIG. 6. In this embodiment, the light source 145 of the imaging catheter assembly 120 is placed on the rear facing end of the auxiliary imaging device 42.

In an additional embodiment of the present invention, the auxiliary imaging device includes a wireless transceiver, associated circuitry and a battery. The wireless transceiver is configured to receive video signals from the imaging unit of the auxiliary imaging device and to transmit them wirelessly to a control box. Alternatively, the wireless circuit may be implemented in a flexible PCB or the handle of the imaging catheter assembly. The control box may also include a wireless transceiver. This wireless transceiver enables the control box to receive wireless video signals from the imaging device and transmit control commands to the imaging device.

The wireless signal transmission and the use of batteries eliminate the need for electrical conductors within the tubular body 36. This reduces the restrictions imposed by electrical conductors to the physician's movements of the endoscope. Additionally, reducing the number of electrical conductors in the catheter and the flex-PCB allows for a larger diameter channel to be included in the catheter.

While the imaging catheter has been described throughout the description as being deployed inside an endoscope, in other applications it may be deployed through other methods such as through a straight tube or cannula, by a flexible insertion tube, or by a guide wire.

The invention claimed is:

1. An endoscope assembly, comprising:
   an endoscope with a first imaging sensor and a first light source; and
   a rear-viewing imaging device with a curved link configured to extend beyond the distal end of the endoscope, the rear-viewing imaging device having a second imaging sensor and a second light source, wherein the second imaging sensor and the second light source face the first imaging sensor, and the second light source is located along a curve of the link,
   wherein the second imaging sensor and the second light source are on when the first imaging sensor and the first light source are off, and wherein the second imaging sensor and the second light source are off when the first imaging sensor and the first light source are on.

2. The endoscope assembly of claim 1, wherein the curved link is made of a shape memory material and has a U-shaped natural configuration.

3. The endoscope assembly of claim 1, wherein the second light source is located along an interior side of the curve.

4. The endoscope assembly of claim 2, wherein the second light source is located at the center of the U-shaped curve of the link.

5. The endoscope assembly of claim 1, wherein the curved link has a plurality of curves.

6. The endoscope assembly of claim 1, further comprising a plurality of light sources located on the link.

7. The endoscope assembly of claim 1, wherein the second light source is an LED.

8. The endoscope assembly of claim 1, wherein the first and second imaging sensors provide views of at least a portion of a same area.

9. The endoscope assembly of claim 8, wherein the first and second imaging sensors provide different views of the same area.

10. The endoscope assembly of claim 1, wherein the first imaging sensor and first light source and the second imaging sensor and second light source are turned on and off at a sufficiently high frequency such that eyes do not sense that they are being intermittently turned on and off.

11. The endoscope assembly of claim 9, wherein the first light source is covered by a first polarizing filter, and the second imaging sensor is covered by a second polarizing filter that blocks light that is transmitted through the first polarizing filter.

12. The endoscope assembly of claim 9, wherein only one of the imaging sensors is covered by a first polarizing filter, and only the light source facing the only one of the imaging sensors is covered by a second polarizing filter that blocks light that is transmitted through the first polarizing filter.

* * * * *